(12) United States Patent
Saigo et al.

(10) Patent No.: US 11,645,859 B2
(45) Date of Patent: May 9, 2023

(54) ANALYSIS DEVICE, ANALYSIS METHOD, ANALYSIS PROGRAM AND DISPLAY DEVICE

(71) Applicants: NIKON CORPORATION, Tokyo (JP); The University of Tokyo, Tokyo (JP)

(72) Inventors: Takuro Saigo, Tokyo (JP); Shinichi Furuta, Yokohama (JP); Shunsuke Takei, Yokohama (JP); Masafumi Yamashita, Fujisawa (JP); Shoko Yamasaki, Tokyo (JP); Masayuki Murata, Tokyo (JP); Fumi Kano, Tokyo (JP); Yoshiyuki Noguchi, Tokyo (JP)

(73) Assignees: NIKON CORPORATION, Tokyo (JP); THE UNIVERSITY OF TOKYO, Tokyo (JP)

( * ) Notice: Subject to any disclaimer, the term of this patent is extended or adjusted under 35 U.S.C. 154(b) by 1104 days.

(21) Appl. No.: 16/312,235

(22) PCT Filed: Jun. 30, 2016

(86) PCT No.: PCT/JP2016/069449
§ 371 (c)(1),
(2) Date: Dec. 20, 2018

(87) PCT Pub. No.: WO2018/003063
PCT Pub. Date: Jan. 4, 2018

(65) Prior Publication Data
US 2019/0236778 A1 Aug. 1, 2019

(51) Int. Cl.
*G06V 10/44* (2022.01)
*G06T 7/00* (2017.01)
(Continued)

(52) U.S. Cl.
CPC .............. *G06T 7/0012* (2013.01); *C12M 1/34* (2013.01); *G01N 33/48* (2013.01); *G06V 10/44* (2022.01);
(Continued)

(58) Field of Classification Search
CPC .. G06T 7/0012; G06V 20/695; G06V 20/698; G06V 10/44
See application file for complete search history.

(56) References Cited

U.S. PATENT DOCUMENTS 9,280,698 B2 3/2016 Kii et al.
2006/0210962 A1 9/2006 Imaizumi et al.

FOREIGN PATENT DOCUMENTS

EP 1672078 A1 6/2006
JP 2005-102538 A 4/2005
(Continued)

OTHER PUBLICATIONS

Aug. 16, 2016 Search Report issued in International Patent Application No. PCT/JP2016/069449.
(Continued)

*Primary Examiner* — Sam Bhattacharya
(74) *Attorney, Agent, or Firm* — Oliff PLC

(57) ABSTRACT

An analysis device configured to analyze a correlation between feature values in a cell in response to a stimulus includes: a cell-image acquiring unit configured to acquire a plurality of cell images in which the cell that is stimulated is captured; a feature value calculating unit configured to calculate a feature value for constituent elements that form the cell, based on the plurality of cell images acquired by the cell-image acquiring unit; a correlation calculating unit configured to use the feature value calculated by the feature value calculating unit and to calculate correlations between the constituent elements; a correlation selecting unit config- (Continued)

ured to select a first correlation from the correlations calculated by the correlation calculating unit; and an image selecting unit configured to select a first cell image from the plurality of cell images that are captured, based on the first correlation that is selected.

28 Claims, 17 Drawing Sheets

(51) Int. Cl.
G01N 33/48 (2006.01)
C12M 1/34 (2006.01)
G06V 20/69 (2022.01)

(52) U.S. Cl.
CPC ............ *G06V 20/69* (2022.01); *G06V 20/695* (2022.01); *G06V 20/698* (2022.01); *G06T 7/0016* (2013.01); *G06T 2207/10056* (2013.01); *G06T 2207/30024* (2013.01)

(56) References Cited

FOREIGN PATENT DOCUMENTS

| JP | 2011-239778 A | 12/2011 |
| WO | 2014/030379 A1 | 2/2014 |
| WO | 2015/182382 A1 | 12/2015 |

OTHER PUBLICATIONS

Aug. 16, 2016 Written Opinion issued in International Patent Application No. PCT/JP2016/069449.
Jan. 7, 2020 Office Action issued in Japanese Patent Application No. 2018-524662.

UI1

☐ FOCUS
☑ SHAPE (DEGREE OF CIRCULARITY) OF IMAGE-CAPTURING TARGET OBJECT
☐ IMAGE-CAPTURING TARGET DOES NOT OVERLAP
☐ IMAGE-CAPTURING TARGET IS NOT PEELED OFF
☐ NO ABNORMALITY EXISTS IN INTERNAL STRUCTURE OF IMAGE-CAPTURING TARGET
☐ APPEARANCE IS EQUAL BETWEEN MEASUREMENT TARGETS IN TERMS OF TIME
☐ NO DUST IS CAPTURED
☐ NUMBER OF IMAGES SELECTED [1] NUMBER OF IMAGES

[CANCEL]   [OK]

☐ RANDOM
☐ AVERAGE VALUE
☐ MEDIAN VALUE
☐ MOST FREQUENT VALUE
☑ MAXIMUM VALUE
☐ MINIMUM VALUE

RANGE OF TOLERANCE
☑ [2] NUMBER OF VALUES
☐ ± [10]
☐ [40] %

[CANCEL]   [OK]

FIG. 6

| Cell# | FEATURE VALUE A |
|---|---|
| 101 | 100 |
| 2 | 100 |
| 23 | 98 |
| 1300 | 97 |
| ⋮ | ⋮ |

FIG. 7

| Cell# | FEATURE VALUE A | FEATURE VALUE B | ... |
|---|---|---|---|
| 101 | 100 | 100 | ... |
| 2 | 100 | 80 | ... |
| 23 | 78 | 98 | ... |
| 1300 | 100 | 75 | ... |
| ⋮ | ⋮ | ⋮ | ⋮ |

FIG. 8

ANALYSIS DEVICE, ANALYSIS METHOD, ANALYSIS PROGRAM AND DISPLAY DEVICE

TECHNICAL FIELD

The present invention relates to an analysis device, an analysis method, an analysis program, and a display device.

BACKGROUND ART

In biological science, medical science, and the like, it is known that there is a correlation, for example, between a state of health, disease, or the like of a living organism; and a state of cells, organelles inside the cells, and the like. Thus, for example, analyzing signaling pathways of information transmitted between cells or within cells can be helpful for research relating to biosensors in industrial applications, in the manufacture of drugs with the aim of preventing disease, and the like. In various analysis techniques relating to cells and tissue slices, techniques are known that use image processing, for example (see Patent Document 1, for example).

CITATION LIST

Patent Literature

Patent Document 1: U.S. Pat. No. 9,280,698

SUMMARY OF INVENTION

Technical Problem

However, in a case where the interaction within cells or between cells is calculated, the number of images containing imaged cells significantly increases, and it takes a lot of effort to select images of cells having a predetermined feature value from among a large number of images containing imaged cells.

The present invention has been made in view of the problem described above, and an object of the present invention is to provide an analysis device, an analysis method, an analysis program, and a display device, which are used to select a predetermined image.

Solution to Problem

According to an aspect of the present invention, an analysis device configured to analyze a correlation in a cell in response to a stimulus includes: a cell-image acquiring unit configured to acquire a plurality of cell images in which the cell that is stimulated is captured; a feature value calculating unit configured to calculate a plurality of types of feature values for respective constituent elements that form the cell, based on the plurality of cell images acquired by the cell-image acquiring unit; a correlation calculating unit configured to use the plurality of types of feature values calculated by the feature value calculating unit and to calculate correlations between the constituent elements; a correlation selecting unit configured to select a first correlation from the correlations calculated by the correlation calculating unit; and an image selecting unit configured to select a first cell image from the plurality of cell images that are captured, based on the first correlation that is selected.

Furthermore, according to another aspect of the present invention, an analysis method for analyzing a correlation in a cell in response to a stimulus includes the steps of: acquiring a plurality of cell images in which the cell that is stimulated is captured; calculating a plurality of types of feature values for respective constituent elements that form the cell, based on the plurality of cell images acquired in the acquiring a plurality of cell images; calculating correlations between the constituent elements using the plurality of types of feature values calculated in the calculating a plurality of types of feature values; selecting a first correlation from the correlations calculated in the calculating correlations; and selecting a first cell image from the plurality of cell images that are captured, based on the first correlation selected in the selecting a first correlation.

Furthermore, according to another aspect of the present invention, an analysis program is for analyzing a correlation in a cell in response to a stimulus, the program includes the steps of: acquiring a plurality of cell images in which the cell is stimulated is captured; calculating a plurality of types of feature values for respective constituent elements that form a cell, based on the plurality of cell images acquired in the acquiring a plurality of cell images; calculating correlations between the constituent elements using the plurality of types of feature values calculated in the calculating a plurality of types of feature values; selecting a first correlation from the correlations calculated in the calculating correlations; and selecting a first cell image from the plurality of cell images that are captured, based on the first correlation selected in the selecting a first correlation.

Advantageous Effects of Invention

According to the present invention, an analysis device, an analysis method, an analysis program, and a display device, which are used to select a predetermined image, are provided.

BRIEF DESCRIPTION OF DRAWINGS

FIG. 5 is a diagram illustrating an example of a screen for selecting an image selection criterion.

FIG. 6 is a diagram illustrating an example of a screen for selecting a selection criterion and a range of tolerance concerning a feature value.

FIG. 7 is a diagram illustrating an example of a feature value in a case where a feature value is selected as an image selection criterion.

FIG. 8 is a diagram illustrating an example of feature values in a case where measurement targets are selected as image selection criteria.

DESCRIPTION OF EMBODIMENTS

First Embodiment

Outline of Configuration of Cell Observation System

Hereinbelow, a cell observation system according to a first embodiment of the present invention will be described with reference to the drawings.

Figure 1:
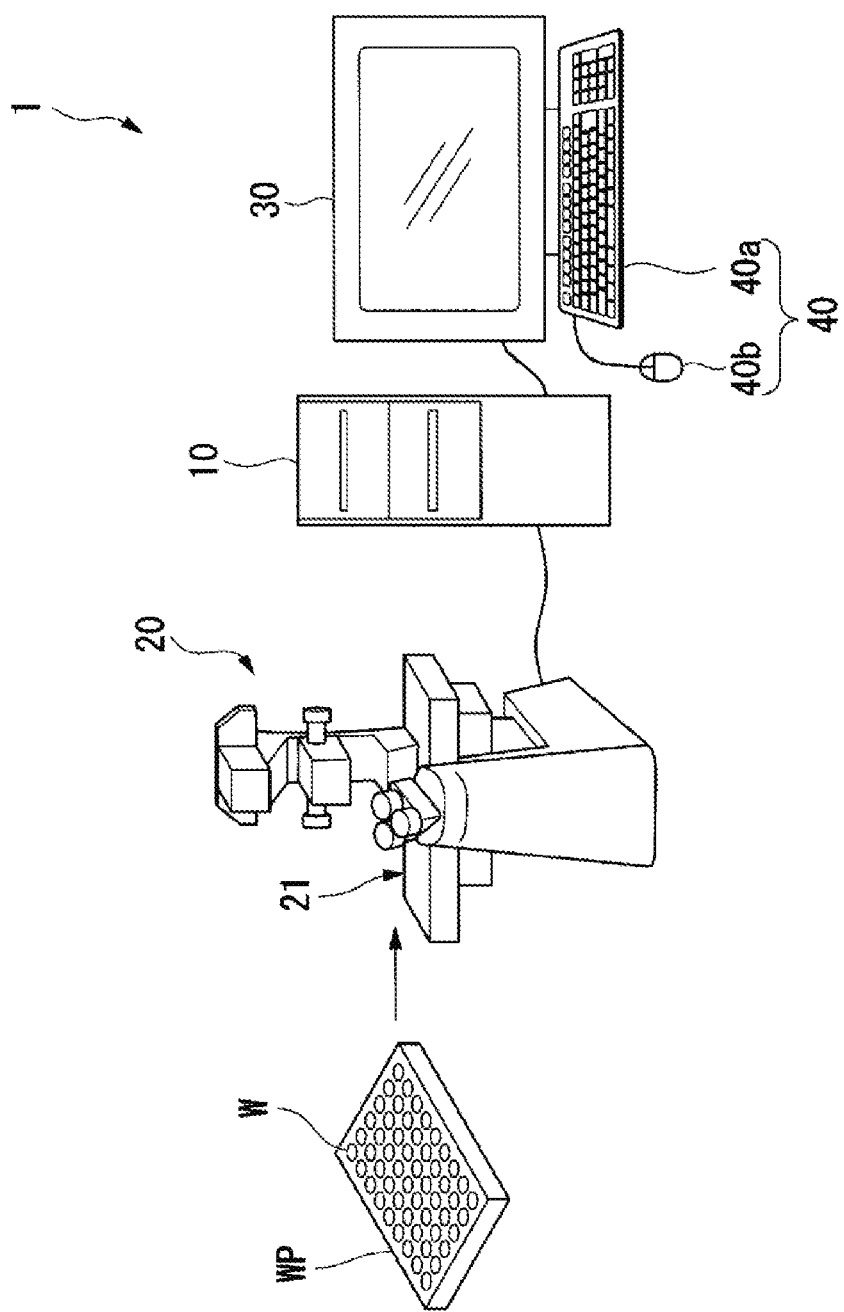
FIG. 1 is a diagram illustrating an external configuration of a cell observation system according to the present embodiment.

FIG. 1 is a diagram illustrating an external configuration of a cell observation system 1 according to the present embodiment.

The cell observation system 1 performs image processing to an image acquired by capturing an image of cells and the like. In the following description, an image acquired by capturing a cell and the like is simply referred to as a captured image. In the captured image, a plurality of cells or the like are imaged. More specifically, the captured image includes a captured image in which a plurality of cells or the like are imaged and a captured image in which one cell or the like is imaged. In other words, the number of cells imaged in the captured image is not limited to one. In addition, the captured image includes images taken with various magnifications. The cell observation system 1 includes an analysis device 10, a microscopic device 20, a display unit 30, and a manipulation unit 40.

The analysis device 10 is a computer device that analyzes the captured image acquired with the microscopic device 20. The analysis device 10 selects an image that a user desires from among a plurality of cell images on the basis of results of analysis of the captured images.

The display unit 30 displays an image such as an image selected by the analysis device 10.

The manipulation unit 40 is operated by a user who selects an image displayed on the display unit 30. Upon user operation, the manipulation unit 40 outputs an operation signal. One example of the manipulation unit 40 includes a keyboard 40a and a mouse 40b.

The microscopic device 20 is a biological microscope and includes an electromotive stage 21 and an image capturing unit 22. The electromotive stage 21 can freely move the position of an image-capturing target object in a predetermined direction (for example, a certain direction in a two-dimensional plane extending in the horizontal direction). The image capturing unit 22 includes an image capturing element such as a Charge-Coupled Device (CCD) and a Complementary MOS (CMOS) and captures an image of an object to be imaged on the electromotive stage 21. Note that the microscopic device 20 may not include the electromotive stage 21, and the stage may be a stage that does not move in a predetermined direction.

More specifically, the microscopic device 20 has, for example, functions of a Differential Interference Contrast Microscope (DIC), a phase contrast microscope, a fluorescence microscope, a confocal microscope, a super-resolution microscope, or a two-photon excitation fluorescence microscope. The microscopic device 20 captures images of the culture vessel placed on the electromotive stage 21. The culture vessel is, for example, a well plate WP. The microscopic device 20 emits light onto cells cultivated within a number of wells W provided in the well plate WP to capture the transmitted light transmitted through the cells, as the image of the cells. In this way, an image of the cells can be obtained, such as a transmission DIC image, a phase contrast image, a dark field image, and a bright field image. In addition, by irradiating the cells with excitation light that excites fluorescent material, an image can be captured of fluorescence emitted from the biological material, as the image of the cells.

In the present embodiment, cells are stained, and the cell images are captured. In the present embodiment, cells are fixed and subjected to immunostaining. Reagents such as formaldehyde are used to perform a process of fixing cells. The cells that have been fixed stop metabolizing. Thus, a plurality of cells need to be prepared in a case where the observation of temporal change within the cell is performed after a stimulus is given to the cell. For example, there is a case where, after a stimulus is given to cells, observation is performed for a change in the cells for a first period and a change in the cells for a second period that is different from the first period. In this case, after the first period elapses, the stimulus is given to the cells, the cells are fixed in order to apply immunostaining to them, and the cell image is acquired. On the other hand, cells, which are different from the cells used for observation for the first period, are prepared, and a stimulus is given to the cells. Then, after the second period elapses, the cells are fixed in order to apply immunostaining to them, and the cell image is acquired. Through these processes, the change within each cell in response to the stimulus is estimated on the basis of the cell image in the first period. In addition, the change within each cell in response to the stimulus is estimated on the basis of the cell image in the second period. Thus, by observing the change in a cell for the first period and the change in the cell for the second period, it is possible to estimate the temporal change in the cell. Furthermore, the number of cells used for observing the changes within a cell for the first period and the second period is not limited to one. Thus, images of a plurality of cells are acquired for each of the first period and the second period. For example, in a case where the number of cells for which changes within the cells are to be observed is 1000, 2000 cells are necessary for the first period and the second period, and 2000 cell images are necessary. Thus, in a case where details of the changes within the cells in response to the stimulus need to be acquired, a plurality of cell images are necessary for each period from when a cell is stimulated to when the cell is imaged, and a large number of cell images are acquired. In other words, the cell image is an image in which changes in a cell in response to a stimulus are captured.

Furthermore, the microscopic device 20 may capture, as the above-described image of the cells, a light or fluorescence emitted from the fluorescent material itself incorporated in a biological material, or an emitted light or fluorescence generated as a result of the combination of a material having a chromophore and a biological material. In this way, the cell observation system 1 can acquire a fluorescence image, a confocal image, a super-resolution image, and an image from a two-photon excitation fluorescence microscope. Note that the method for acquiring an image of a cell is not limited to a method using the optical microscope. For example, an electron microscope may be used. In addition, for the image containing a cell, which will be described later, an image obtained through another method may be used to acquire a correlation. In other words, the type of an image containing a cell may be selected as appropriate. The cell as used in the present embodiment includes, for example, a primary cultured cell, a cultured cell line, and a cell obtained through tissue sectioning. To observe a cell, a group of cells, a tissue sample, an organ, or an individual (such as an animal) may be used as a sample to be observed for observation to acquire an image containing the cell. Note that the state of the cells is not particularly limited to a specific state. They may be in a living state or may be in a fixed state, and may be one of either "in-vivo" or "in-vitro". In addition, it may be possible to combine information on the living state with information on the fixed state.

The state of the cell may be selected as appropriate depending on purposes. For example, selection may be made between fixing and not fixing depending on types (for example, protein and organelle) to be discerned in a structure within a cell. In addition, in a case where the dynamical behavior of a cell is acquired from a fixed cell, a plurality of fixed cells are prepared under different conditions to acquire the dynamical behavior. In the structure within a cell, the type to be discerned is not limited to those inside a nucleus.

In addition, to observe a cell, the cell may be observed after the cell is processed in advance. Of course, to observe a cell, the cell may be observed in a state where the cell is not processed. In a case where a cell is observed, the cell may be stained through immunostaining to be observed. For example, a stain solution to be used may be selected depending on types to be discerned in an intranuclear structure within a cell. In addition, various staining methods may be used for the staining method. For example, it may be possible to use various types of special staining used mainly for staining of tissues, or hybridization using the binding of nucleic acid sequence.

Furthermore, the cell may be processed through light-emission or using fluorescent protein (for example, light emission or fluorescent protein obtained through manifestation from introduced gene (green fluorescent protein, GFP)) to perform observation. For example, the light-emission or fluorescent protein used may be selected depending on types to be discerned in an intranuclear structure within a cell.

Furthermore, it may be possible to select the pre-processing for analyzing correlation acquisition such as a method for observing the cell or a method for staining the cell, as appropriate depending on purposes. For example, dynamic information on a cell may be acquired through a method appropriate for a case where the dynamic behavior of the cell is obtained, and information on signal transmission in the cell may be acquired through a method appropriate for a case where signal transmission in the cell is obtained. These pieces of pre-processing selected depending on purposes may differ from each other. In addition, it may be possible to decrease the number of types of pre-processing selected depending on purposes. For example, in a case where the appropriate method differs between the method for acquiring the dynamic behavior of a cell and the method for acquiring signal transmission in the cell, this complicates the acquisition of different pieces of information using different methods. Thus, rather than choosing the appropriate method, the pre-processing can be performed with a common method in a case where the common method is satisfactory for acquiring each information.

The well plate WP includes a plurality of wells W. In this example, the well plate WP includes 96 (12×8) wells W. Cells are cultivated in the wells W under specific experimental condition. The specific experimental condition includes a temperature, a humidity, the cultivation period, an elapsed time period from when a stimulus is applied, a type of stimulus applied, the type, the strength, the density, the amount, the existence or absence of a stimulus, and the induction of biological characteristics. The stimulus is, for example, a physical stimulus such as electricity, sound waves, magnetism, or light; or a chemical stimulus obtained by administering a substance, a drug, or the like. Further, the biological characteristics are features indicating a stage of differentiation of the cells, a morphology, the number of the cells, and the like.

Functional Configuration of Analysis Device 10

Next, the configuration of the analysis device 10 will be described with reference to FIG. 2.

Figure 2:
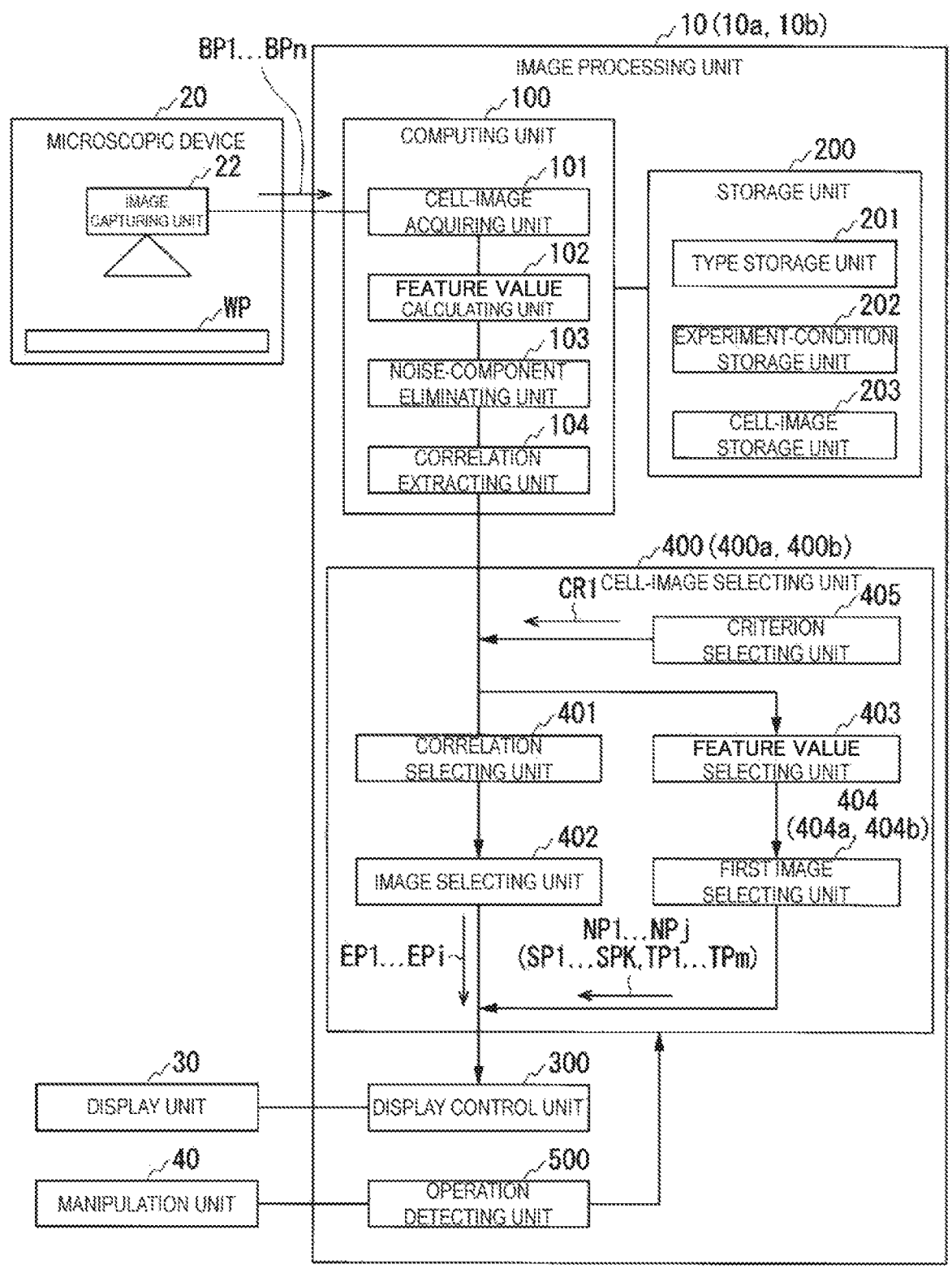
FIG. 2 is a diagram illustrating an example of the configuration of an analysis device according to the present embodiment.

FIG. 2 is a diagram illustrating an example of the configuration of the analysis device 10 according to the present embodiment.

The analysis device 10 includes an operation detecting unit 500, a computing unit 100, a storage unit 200, a display control unit 300, and a cell-image selecting unit 400.

The operation detecting unit 500 detects an operation signal outputted by the manipulation unit 40. The operation detecting unit 500 outputs the detected operation signal to the cell-image selecting unit 400.

The computing unit 100 functions with a processor executing a program stored in the storage unit 200. In addition, some or all of each of these functional portions in the computing unit 110 may be configured by hardware such as a Large Scale Integration (LSI) and an Application Specific Integrated Circuit (ASIC).

The computing unit 100 includes a cell-image acquiring unit 101, a feature value calculating unit 102, a noise-component eliminating unit 103, and a correlation extracting unit 104.

The cell-image acquiring unit 101 acquires a captured image BP captured by the image capturing unit 22 and supplies the feature value calculating unit 102 with the acquired cell image. Here, the cell image acquired by the cell-image acquiring unit 101 includes a plurality of images in which states of cultivation of cells are captured in a time series and a plurality of images in which cells are cultivated under various experimental conditions. In addition, the captured image BP includes a plurality of captured images. More specifically, the captured image BP includes images from a captured image BPl to a captured image BPn. Here, the character "n" in the captured image BPn represents an integer equal to or greater than one.

The feature value calculating unit 102 calculates a plurality of types of feature values in the cell images supplied by the cell-image acquiring unit 101. The feature value in the cell image includes, for example, the luminosity of the cell image, the area of a cell in the image, and the dispersion of luminosity of the cell image in the image. In other words, it is a feature obtained from the information acquired from the captured cell image. For example, the luminance distribution in the acquired image is calculated. A plurality of time series images or a plurality of images in which the state of a cell varies by differentiation are used. Locational information indicating a change in luminosity, which is different from others, is obtained on the basis of a change in the calculated luminosity distribution over a predetermined period of time, or a change in association with a change in the state of a cell such as differentiation of the calculated luminosity distribution; and the change in luminosity may be set as the feature value. In this case, it is not limited to the change of time, and it may be possible to use a plurality of images in which changes in states of a cell such as differentiation differs from each other. In addition, the information on location indicating a change in different luminosities may be used as the feature value. For example, it may be possible to use the behavior of a cell in a predetermined period of time, or the behavior in association with a change in states of the cell such as cell differentiation, or it may be possible to use a change in the shape of a cell in a predetermined period of time, or a change in association with a change in states of the cell such as differentiation of the shape of the cell. Furthermore, in a case where no change in the predetermined period of time or no change in association with a change of states of the cell such as differentiation can be found from the captured cell image, such no change may be regarded as the feature value. In other words, the feature value calculating unit 102 calculates, on the basis of the plurality of acquired cell images, a change in the feature value concerning a constituent element of a cell captured in a captured image.

The noise-component eliminating unit 103 eliminates a noise component (noise) from the feature value calculated by the feature value calculating unit 102.

The correlation extracting unit 104 extracts a plurality of correlations between feature values calculated by the feature value calculating unit 102, on the basis of the likelihood of the feature values from the feature values for which noise components have been already removed by the noise-component eliminating unit 103. Here, the likelihood represents a value indicating a likelihood of a predetermined condition estimated on the basis of a result calculated in accordance with this predetermined condition. In addition, the likelihood is a cost function for representing a likelihood of a parameter to be estimated in a case where data follow a stochastic model.

In other words, the computing unit 100 computes a plurality of types of feature values of cell images on the basis of the cell images in which cells are captured. The computing unit 100 uses the cell images in which cells are captured, to extract the plurality of types of feature values in the cell images, and computes whether extracted feature values change in a correlated manner with each other. In other words, the computing unit 100 calculates feature values that change in a correlated manner in association with a change in a predetermined feature value. The computing unit 100 computes that a correlation exists in a case that changes in feature values are correlated as a result of the calculation of feature values. The computing unit 100 supplies the cell-image selecting unit 400 with cell images in which cells are captured, a plurality of types of computed feature values in the cell images, and a plurality of relationships of computed correlation between the feature values. In addition, the computing unit 100 may supply the display control unit 300 with results of computation. Note that, in a case where feature values are correlate with each other, it may be said that they have a correlation.

The cell-image selecting unit 400 includes a correlation selecting unit 401, an image selecting unit 402, a feature value selecting unit 403, a first image selecting unit 404, and a criterion selecting unit 405.

The correlation selecting unit 401 selects a first correlation from a plurality of correlations between feature values supplied from the computing unit 100.

The image selecting unit 402 selects, on the basis of the first correlation, a correlation cell image EP indicating a correlation from the plurality of cell images in which cells are captured, the cell images being supplied from the computing unit 100. The image selecting unit 402 extracts a correlation cell image EP used to calculate the selected first correlation. In this case, the correlation cell image EP indicating a correlation includes a plurality of correlation cell images EP indicating correlations. More specifically, the correlation cell image EP indicating a correlation includes images from a correlation cell image EP1 indicating a correlation to a correlation cell image EPi indicating a correlation. Here, the character "i" in the correlation cell image EPi indicating a correlation represents an integer equal to or greater than one. The image selecting unit 402 supplies the display control unit 300 with the selected cell image.

The feature value selecting unit 403 selects a first feature value from a plurality of types of feature values in the cell images supplied from the computing unit 100.

The first image selecting unit 404 selects, on the basis of the first feature value, a cell image NP from the plurality of cell images in which cells are captured, the cell images being supplied from the computing unit 100. The first image selecting unit 404 extracts a cell image NP used to calculate the first feature value to be selected. The cell image NP includes a plurality of cell images NP. More specifically, the cell image NP includes images from a cell image NP1 to a cell image NPj. Here, the character "j" in the cell image NPj represents an integer equal to or greater than one. The first image selecting unit 404 supplies the display control unit 300 with the selected cell image.

The criterion selecting unit 405 selects an image selection criterion CR1. The criterion selecting unit 405 outputs the selected image selection criterion CR1 to the image selecting unit 402 and the first image selecting unit 404. The image selecting unit 402 and the criterion selecting unit 405 acquire the image selection criterion CR1 from the criterion selecting unit 405. The image selecting unit 402 and the first image selecting unit 404 select a cell image on the basis of the image selection criterion CR1. The image selection criterion CR1 represents a criterion indicating the state of a cell image. More specifically, the state of a cell image indicates the number of cells in an image, whether the cell is separately captured, the shape of the captured image, the presence or absence of foreign matter in the captured image, the contrast of the cell image, and the state of a difference between the cell and the position of the focal point of the image capturing device. Whether the cell is separately captured means whether the cell is captured so as to overlap with other cell. In addition, the image selection criterion CR1 includes the degree of feature value and a criterion concerning the number of cell images that the cell-image selecting unit 400 selects. The foreign matter represents, for example, a matter different from any cell captured in an image. For example, it includes foreign matter incorporated when a sample for measurement is prepared. The foreign matter includes an inorganic substance, an organic substance, or a combination of an inorganic substance and an organic substance. Furthermore, as the foreign matter, in a case where a predetermined cell is to be observed, a cell that belongs to a type different from that of the predetermined cell may be treated as the foreign matter. In addition, the contrast of a cell image represents a difference in at least one of color, brightness, and luminosity between a cell captured into a cell image and a portion other than the cell captured in the cell image. In addition, the contrast of a cell image represents a difference in at least one of color, brightness, and luminosity between a certain cell image and another cell image different from the certain cell image.

The result output unit 300 outputs a result of computation performed by the computing unit 100 to the display unit 30. The display control unit 300 outputs the cell image that the cell-image selecting unit 400 selects, to the display unit 30. In other words, the display control unit 300 causes the display unit 30 to display, as a display image, the cell image that the cell-image selecting unit 400 selects. Note that the result output unit 300 may output a result of computation performed by the computing unit 100 or the cell image that the cell-image selecting unit 400 selects, to an output device other than the display unit 30 or a storage device.

The display unit 30 displays the result of computation outputted by the result output unit 300.

The specific operation procedure of the analysis device 10 described above will be described with reference to FIG. 3.

Figure 3:
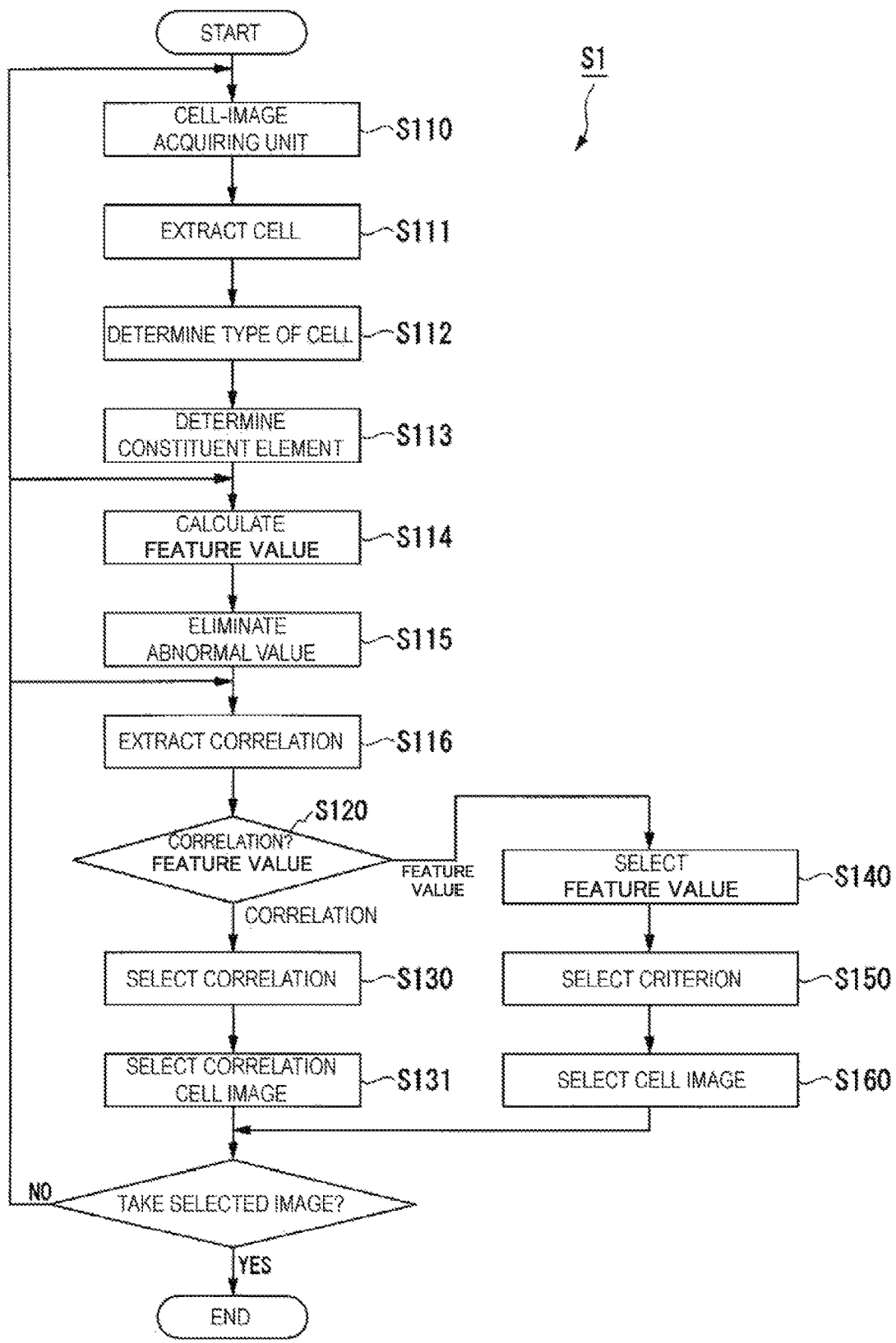
FIG. 3 is a flowchart illustrating an example of an operation procedure of an analysis device according to the present embodiment.

Example of Operation Performed by Analysis Device 10 According to First Embodiment FIG. 3 is a flowchart S1 illustrating an example of an operation procedure performed by the analysis device 10 according to the present embodiment. Note that the operation procedure described here is merely an example, and it may be possible to omit the operation procedure or add another operation procedure.

The cell-image acquiring unit 101 acquires a cell image (step S110). The cell is fixed and stained, and hence, the cell image contains information concerning elements that form a cell. For example, an image of a plurality of types of biological tissue having a different size such as a gene, protein, and an organelle is contained. In addition, the cell image includes information on the shape of a cell. Furthermore, dynamic behavior is acquired from the time series cell images or cell images in which the states of the cell are different from each other by differentiation. Thus, an analysis is performed using a plurality of different sizes of scale from the fine structure within a cell to the shape of the cell, or scales in different dimensions as to cell images, which are in different time series or in different states of cell caused by differentiation from cell images in a certain period of time or in certain states of cell caused by differentiation, and hence, it may be possible to call the procedure a multi-scale analysis.

The feature value calculating unit 102 extracts, for each cell, an image of a cell contained in the cell image acquired in the step S110 (step S111). The feature value calculating unit 102 performs image processing to the cell image using a known method to extract an image of a cell. In this example, the feature value calculating unit 102 performs the outline extraction of an image or pattern matching to extract an image of a cell.

Next, the feature value calculating unit 102 determines the type of a cell contained in the image of the cell extracted in step S111 (step S112). Furthermore, the feature value calculating unit 102 determines, on the basis of the result of determination in step S112, the constituent element of the cell contained in the image of the cell extracted in step S111 (step S13). Here, the constituent element of the cell includes organelles such as the cell nucleus, lysosome, Golgi body, and mitochondria, and protein that forms the organelle. Note that, although the type of the cell is determined in step S112, the type of the cell may not be determined. In this case, in a case where the type of the cell introduced has already been determined, such information may be used. Of course, the type of the cell may not be identified.

Next, the feature value calculating unit 102 calculates a feature value in the image for each constituent element of the cell determined in step S113 (step S114). The feature value includes the luminosity value of a pixel, the area of a certain region in the image, and the dispersion value of luminosity of the pixel. In addition, the feature value has a plurality of types corresponding to constituent elements of the cell. As one example, the feature value in the image of a cell nucleus includes an intra-nuclear total luminance value and the area of the nucleus. The feature value in the image of a cytoplasm includes the total luminance value in the cytoplasm and the area of the cytoplasm. In addition, the feature value in the image of the entire cell includes an intra-cellular total luminance value and the area of the nucleus. Furthermore, the feature value in the image of a mitochondria includes the rate of fragmentation. Note that the feature value calculating unit 102 may calculate the feature value through normalization into, for example, a value ranging from zero to one.

In addition, the feature value calculating unit 102 may calculate the feature value on the basis of information on experimental conditions for a cell associated with the cell image. For example, in a case where a cell is caused to react with antibodies and the cell image is captured, the feature value calculating unit 102 may calculate a feature value specific to the case of reaction with antibodies. Furthermore, in a case where a cell is stained or fluorescent protein is given to the cell, and the cell image is captured, the feature value calculating unit 102 may calculate a feature value specific to the case where the cell is stained or the case where fluorescent protein is given to the cell.

In these cases, the storage unit 200 may include an experiment-condition storage unit 202. This experiment-condition storage unit 202 stores, for each cell image, information on experimental conditions for a cell associated with the cell image.

The feature value calculating unit 102 supplies the noise-component eliminating unit 103 with the feature value calculated in step S114.

The noise-component eliminating unit 103 eliminates a noise component from the feature value calculated in step S114 (step S115). More specifically, the noise-component eliminating unit 103 acquires information indicating a normal range or abnormal range of the feature value. The information indicating the normal range or abnormal range of the feature value is set in advance on the basis of a property of the cell captured in the cell image. For example, of feature values in an image of a cell nucleus, the normal range for the intra-nuclear total luminance value is set on the basis of the property of the image of the cell nucleus. In a case where the calculated feature value does not fall in the normal range, the noise-component eliminating unit 103 eliminates this feature value as a noise component. Here, in a case where the feature value is eliminated as a noise component, the noise-component eliminating unit 103 eliminates it for each cell. More specifically, there is a case where a plurality of feature values are calculated for a certain cell. For example, there is a case where, for the certain cell, the intra-cellular total luminance value, the intra-nuclear total luminance value, and the area of the nucleus are calculated as the feature values. In this case, in a case where the intra-cellular total luminance value is eliminated for the certain cell as the noise component, the noise-component eliminating unit 103 also eliminates the intra-nuclear total luminance value and the area of the nucleus for the cell. In other words, in a case where, of the plurality of feature values calculated for a certain cell, at least one of the feature values does not fall in the normal range, the noise-component eliminating unit 103 also eliminates the other feature values of the cell.

In other words, the noise-component eliminating unit 103 eliminates, for each cell captured in the cell image, the noise component from the feature values supplied to the correlation extracting unit 104, on the basis of information indicating the property of the cell captured in the cell image. With such a configuration, in a case where a certain feature value has a relatively low reliability, the noise-component eliminating unit 103 can eliminate the feature value in a unit of cell. In other words, the noise-component eliminating unit 103 enables the reliability of feature values to be improved.

In addition, in a case where the calculated feature value falls in the normal range, the noise-component eliminating unit 103 supplies the correlation extracting unit 104 with this feature value. Note that the noise-component eliminating unit 103 is not an essential constituent element and may be omitted depending on states of the cell image or states of the calculation of feature values. In this case, the feature value calculating unit 102 supplies the correlation extracting unit 104 with the calculated feature value.

The correlation extracting unit 104 acquires a feature value after the noise component has been eliminated in step S115. This feature value has been calculated for each cell by the feature value calculating unit 102 in step S114. The correlation extracting unit 104 computes whether feature values calculated by the feature value calculating unit 102 change in a correlated manner to each other and extracts the correlation (step S116).

The computing unit 100 supplies the cell-image selecting unit 400 with a feature value after the noise component has been eliminated in step S115. Note that the computing unit 100 may supply the cell-image selecting unit 400 with the feature value calculated in step S114.

In addition, the computing unit 100 supplies the cell-image selecting unit 400 with the correlation extracted in step S116.

One example of the feature value and the correlation will be described with reference to FIG. 4.

Figure 4:
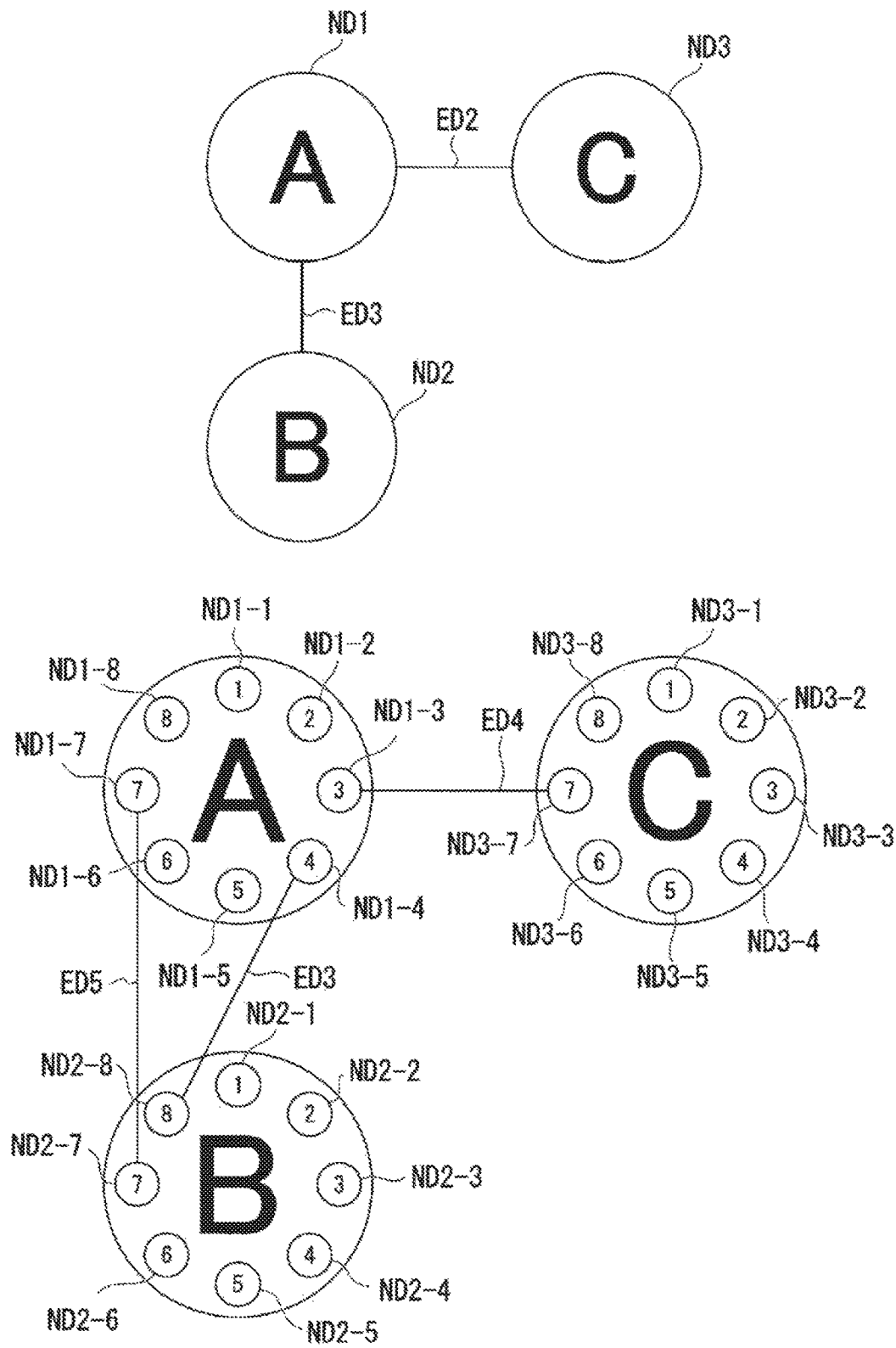
FIG. 4 is a diagram illustrating examples of feature values and correlations.

FIG. 4 is a diagram illustrating examples of feature values and correlations.

A node ND includes protein A (ND1) serving as a measurement target, protein B (ND2) serving as a measurement target, and protein C (ND3) serving as measurement target, as illustrated as circles in FIG. 4. In the present embodiment, correlation measurement between proteins is the objective. Of course, the target of correlation measurement is not limited to protein. A correlation between elements that form a cell may be possible as a measurement target. Examples of the elements include organelle such as the cell nucleus, lysosome, Golgi body, and mitochondria, and protein that forms the organelle. In addition, for the correlation measurement, a correlation between elements belonging to the same type such as between proteins is measured. However, it may be possible to measure a correlation between elements belonging to different types such as between protein and a cell nucleus. Furthermore, the elements that form a cell may be a cell, and of course, a correlation between cells or correlation between a cell and protein may be set as a measurement target. Next, the node ND includes a feature value 1 ND1-1, a feature value 2 ND1-2, a feature value 3 ND1-3, a feature value 4 ND1-4, a feature value 5 ND1-5, a feature value 6 ND1-6, a feature value 7 ND1-7, and a feature value 8 ND1-8. Feature values included in the node ND include the luminosity value of a pixel, the area of a certain region in the image, and the dispersion value of luminosity of the pixel, described above. In other words, in the present embodiment, for the node ND of the protein A, the luminosity value of a pixel of the protein A, the area of the protein A in the pixel, and the luminance value of the protein A at a predetermined position, and the like are included. As with the protein A, for the protein B, features from a feature value 1 ND2-1 to a feature value 8 ND2-8 are given. As with the protein A, for the protein C, features from a feature value 1 ND3-1 to a feature value 8 ND3-8 are given as the node ND.

An edge ED represents a relationship that connects a node ND and a node ND. With the edge ED, relationships of the connected nodes ND are correlated. In the present embodiment, the edge ED connected to the correlating nodes ND is illustrated with lines. Thus, in the present embodiment, it can be understood that the nodes ND that are not connected with any line have a low correlation in relation to the edges ED illustrated with lines. For example, a change in the node ND1-4 and a change in the node ND2-8 synchronize with each other for a predetermined period of time after a predetermined stimulus is given to a protein. For example, the node ND2-8 changes upon the change in the node ND1-4. Alternatively, the node ND1-4 changes, and after this change ends, the node ND2-8 starts to change. Furthermore, in the present embodiment, the number of nodes ND that connects the protein A and the protein B is not limited to one, and there are a plurality of such nodes. The edge ED includes an edge ED1 indicating a correlation between the protein A (ND1) and the protein B (ND2), and an edge ED2 indicating a correlation between the protein A (ND1) and the protein C (ND3), as illustrated as lines that connect feature values in FIG. 4. In addition, the edge ED includes an edge ED3 indicating a correlation between a feature value 4 ND1-4 contained in the protein A and a feature value 8 ND2-8 contained in the protein B; an edge ED4 indicating a correlation between a feature value 3 ND1-3 contained in the protein A and a feature value 7 ND3-7 contained in the protein C; and an edge ED5 indicating a correlation between a feature value 7 ND1-7 contained in the protein A and a feature value 7 ND2-7 contained in the protein B. Furthermore, the degree of correlation of each of the edges ED that connect these pluralities of feature values may be different from each other or may be equal to each other.

The analysis device 10 selects a node ND or edge ED on the basis of an operation signal (step S120).

One Example of Operation in a Case where Correlational Relationship is Selected

A description will be made of a case where the analysis device 10 selects an image based on an edge in step S120. In other words, a description will be made of a case where a user selects an edge that connects nodes ND. In this case, by selecting an edge, the user selects two types of nodes that are connected. Here, two types of nodes include a first constituent element and a second constituent element. The correlation selecting unit 401 selects a change in the first feature value concerning the first constituent element and a change in the second feature value concerning the second constituent element to select a first correlation.

The correlation selecting unit 401 included in the cell-image selecting unit 400 acquires a plurality of correlations extracted in step S116.

The correlation selecting unit 401 outputs the acquired correlations to the display control unit 300. The display control unit 300 causes the display unit 30 to display the acquired correlations. The user operates the manipulation unit 40 to select a correlation displayed on the display unit 30. The operation detecting unit 500 detects the correlation selected by the user. The operation detecting unit 500 outputs the detected correlation to the correlation selecting unit 401.

The correlation selecting unit 401 outputs, to the image selecting unit 402, the correlation detected by the operation detecting unit 500 as a first correlation (step S130).

The image selecting unit 402 acquires the first correlation from the correlation selecting unit 401. The image selecting unit 402 selects a correlation cell image EP from captured images BP on the basis of the first correlation (step S131). The user selects whether the correlation cell image EP selected by the image selecting unit 402 is an image indicating a desired correlation (step S132). In a case where the user judges that the correlation cell image EP is not appropriate for indicating the correlation or that the number of correlation cell images EP selected is small and is not appropriate for comparison, NO is selected. In this case, the analysis device 10 may redo the processes from the calculation of a feature value in step 114, or may redo the processes from the extraction of a correlation in step S116. In addition, the analysis device 10 may redo the processes from the acquisition of a cell image in step 110. In this case, the user may change image capturing conditions for acquiring a cell image to redo the process. Furthermore, in this case, for example, the user may change an adjustment condition of a cell for which a cell image is acquired, to redo the process. In this case, for example, the user may prepare another cell instead of the cell prior to redoing, change the adjustment condition, that is, a stain condition used for staining the cell, and redo the process (NO in step S132). In a case where the user judges that the correlation cell image EP is appropriate for indicating the correlation, the analysis device 10 terminates the process (YES in step S130).

The cell observation system 1 includes the analysis device 10. The analysis device 10 includes the computing unit 100, the cell-image selecting unit 400, and the display control unit 300. The computing unit 100 includes: the cell-image acquiring unit 101 that acquires a cell image (captured image BP) in which a cell is captured; the feature value calculating unit 102 that calculates a plurality of types of nodes ND in the captured image BP acquired by the cell-image acquiring unit 101; and the correlation extracting unit 104 that extracts a specific edge ED from among a plurality of edges ED between the nodes ND calculated by the feature value calculating unit 102. The cell-image selecting unit 400 includes a correlation selecting unit 401 and an image selecting unit 402. The correlation selecting unit 401 selects, on the basis of selection by the user, a first correlation from the edges ED extracted by the correlation extracting unit 104. The image selecting unit 402 selects a correlation cell image EP from the plurality of captured images BP on the basis of the first correlation selected by the correlation selecting unit 401. The analysis device 10 may select a correlation cell image EP that indicates a correlation desired by the user, from among the plurality of captured images BP. With the configuration described above, the user can obtain an image indicating a desired correlation.

One Example of Operation in a Case where Feature Value is Selected

Next, a description will be made of a case where the analysis device 10 selects an image on the basis of feature values in step S120.

The feature value selecting unit 403 included in the cell-image selecting unit 400 acquires a feature value after the noise component has been eliminated in step S115, or a feature value calculated in step S114.

The feature value selecting unit 403 outputs the acquired feature value to the display control unit 300. The display control unit 300 causes the display unit 30 to display the acquired feature value. The user operates the manipulation unit 40 to select a feature value displayed on the display unit 30. The operation detecting unit 500 detects the feature value selected by the user. The operation detecting unit 500 outputs the detected feature value to the feature value selecting unit 403.

The feature value selecting unit 403 outputs the feature value detected by the operation detecting unit 500 to the first image selecting unit 404 as a first feature value (step S140). Note that, in a case where the user selects two feature values, the feature value selecting unit 403 outputs the two selected feature values as a first feature value and a second feature value. In this case, the first image selecting unit 404 sets the first feature value as the first constituent element. The first image selecting unit 404 sets the second feature value as the second constituent element. The first image selecting unit 404 selects the first constituent element and the second constituent element to select a first correlation.

The cell-image selecting unit 400 outputs an image selection criterion CR1 to the display control unit 300. The display control unit 300 causes the display unit 30 to display the acquired image selection criterion CR1. The user operates the manipulation unit 40 to select the image selection criterion CR1 displayed on the display unit 30. The operation detecting unit 500 detects the image selection criterion CR1 selected by the user. The operation detecting unit 500 outputs the detected image selection criterion CR1 to the correlation selecting unit 401 and the feature value selecting unit 403 (step S150).

One Example of Operation for Selecting Image Selection Criterion CR1

With reference to FIGS. 5 to 9, a description will be made of one example in which an image selection criterion CR1 is selected in step S150.

FIG. 5 is a diagram illustrating an example of a screen for selecting an image selection criterion CR1.

The criterion selecting unit 405 gives the display control unit 300 an instruction to display a screen UI1 after a node ND is selected. The display control unit 300 causes the display unit 30 to display the screen UI1.

The user selects the image selection criterion CR1 displayed on the screen UI1.

The image selection criterion CR1 represents a criterion concerning an image in which cells are captured. The criterion concerning an image in which a cell is captured includes a condition for image capturing under which the cell is captured, a condition for a cell concerning the cell to be captured, and a condition for acquiring an image to be captured. In other words, the criterion concerning the image in which the cell is captured is information on the cell captured in the cell image.

The displayed condition for image capturing includes whether the cell to be captured and the focal position of the objective lens are matched. For example, this is displayed as "Focus" on the screen UI1. In addition, the displayed condition includes whether the image to be captured contains any foreign matter other than the cell. For example, this is displayed as "No dust is captured" on screen UI1.

The displayed condition for image capturing includes whether the shape of the cell serving as the image-capturing target has a predetermined shape. For example, the displayed condition for image capturing includes whether the cell has a shape close to the circular shape. For example, this is displayed as "Shape (degree of circularity) of image-capturing target object" on the screen UI1. The displayed condition for image capturing includes whether the image-capturing target is held in a well plate. This is displayed as "Image-capturing target is not peeled off" on the screen UI1. The displayed condition for image capturing includes whether the cell to be captured is in a normal state. The displayed condition for image capturing includes whether the internal structure of the cell to be captured is in an abnormal state. This is displayed as "No abnormality exists in the internal structure of the image-capturing target" on the screen UI1. In addition, the displayed condition for image capturing includes whether the cell is captured so as to overlap with another cell. This is displayed as "Image-capturing target does not overlap" on the screen UI1. In addition, in a case where different cells are fixed, and the plurality of fixed cells are used to acquire an edge ED, images containing captured cells with a similar shape of the plurality of fixed cells are selected. This is displayed as "Appearance is equal between measurement targets in terms of time" on the screen UI1.

As conditions for acquiring the captured image, the number of images acquired may be selected. This is displayed as "Number of images selected" on the screen UI1. FIG. 5 is a diagram illustrating an example of a screen for designating an image selection criterion CR1. Note that the image selection criterion CR1 selected on the screen UI1 is merely one example and is not limited to this.

In a case where the "Focus" is selected by a user, the criterion selecting unit 405 adds it to the image selection criterion CR1 as one criterion for selecting an image in which the focus is on the captured cell.

In a case where the "Shape (degree of circularity) of image-capturing target object" is selected by a user, the criterion selecting unit 405 adds it to the image selection criterion CR1 as one criterion for selecting an image that contains an image-capturing target object having a circular shape. Note that the criterion selecting unit 405 may receive designation of the degree of circularity.

In a case where the "Image-capturing target does not overlap" is selected by a user, the criterion selecting unit 405 adds it to the image selection criterion CR1 as one criterion for selecting an image in which the image-capturing target is captured so as not to overlap.

In a case where the "No abnormality exists in the internal structure of the image-capturing target" is selected by a user, the criterion selecting unit 405 adds it to the image selection criterion CR1 as one criterion for selecting an image that does not have any abnormalities in the internal structure of the image-capturing target.

In a case where the "Appearance is equal between measurement targets in terms of time" is selected by a user, the criterion selecting unit 405 adds it to the image selection criterion CR1 as one criterion for selecting an image in which a change in appearance due to temporal change is equal between measurement targets selected on the screen UI1. In other words, in a case where a fixed cell is used, cells in an image used differ due to temporal change. Thus, cells in an image used differ from time to time, and hence, cells having similar shapes to each other are selected.

In a case where the "No dust is captured" is selected by a user, the criterion selecting unit 405 adds it to the image selection criterion CR1 as one criterion for selecting an image in which no dust such as lint is captured in the image.

In a case where the "Number of images selected" is selected by a user, the criterion selecting unit 405 receives designation of the number of selected images selected by the first image selecting unit 404 and adds it to the image selection criterion CR1 as one criterion for selecting an image.

FIG. 6 is a diagram illustrating an example of a screen UI2 for selecting a selection criterion and a range of tolerance concerning a feature value.

The feature value calculating unit 102 extracts a feature value from cells captured by the image capturing unit 22. Information corresponding to the size of the extracted feature value corresponds to a captured cell image. The size of the amount of change, in response to a stimulus, in a feature value in a cell image corresponds to the cell image. For example, in a case where the area of a cell in a cell image increases in response to a stimulus, the increase in the area corresponds to the cell image. Thus, a cell image can be extracted from a plurality of cell images on the basis of the amount of change in the feature value. In addition, a cell image can be extracted from a plurality of cell images on the basis of the size of the feature value. Thus, the amount of change in the extracted feature value varies, for example, according to individual cells. Even within the same cell, the size of the amount of change varies depending on the type of the feature value. The criterion selecting unit 405 gives the display control unit 300 an instruction to display a screen UI2 as illustrated in FIG. 8 after an image selection criterion CR1 is selected on the screen UI. The display control unit 300 causes the display unit 30 to display the screen UI2.

A user selects a selection criterion for the feature value displayed on the screen UI2 to additionally select an image selection criterion CR1.

The screen UI2 is one example of a screen for designating an image selection criterion CR1 such as "Random" (random value), "Average value", "Median value", "Most frequent value", "Maximum value", and "Minimum value", each of which serves as a range of values contained in the first feature value, "How many values are taken", which serves as the setting for a range of tolerance, "±value", which serves as the value, "What percentage", which serves as a percentage, and the like. Note that the image selection criterion CR1 selected on the screen UI2 is merely one example and is not limited to this.

In a case where "Random" is selected by a user, the criterion selecting unit 405 randomly acquires any image containing a feature value having any value. This enables the user to randomly select an image displayed on the screen. In the present embodiment, in a case where the random is selected, the manipulation unit 40 causes the criterion selecting unit 405 to randomly select an image from a plurality of cell images extracted by the correlation extracting unit 104 from among the cell images captured by the image capturing unit 22.

In a case where the user selects "Average value", the criterion selecting unit 405 adds a criterion to the image selection criterion CR1 so that an image indicating the average value is acquired from images having various feature values. In the present embodiment, the sizes of feature values in individual image are extracted from a large number of extracted captured images BP; the average value of the sizes of feature values in a large number of the captured images is calculated; and an image with the average value or a value close to the average value is displayed. In a case where there are a plurality of images that have the average value or a value close to the average value, the analysis device 10 may display the plurality of images, or may display one of them.

In a case where the user selects "Median value", the criterion selecting unit 405 adds a criterion to the image selection criterion CR1 so that an image indicating the median value is acquired from images having various feature values. The median value may be a value sitting at the center of a histogram created on the basis of the sizes of feature values and the frequency of each of the sizes. For example, the frequency of each of the sizes is the number of cells indicating the feature value. In addition, for example, the frequency of each of the sizes is the number of constituent elements of cells indicating the feature value. The analysis device 10 creates the histogram on the basis of a large number of extracted cell images.

In a case where the user selects "Most frequent value", the criterion selecting unit 405 adds a criterion to the image selection criterion CR1 so that an image indicating the most frequent value is acquired from images having various feature values. For example, in a case where the number of cells having a size of each feature value is counted, the most frequent value means the size of the feature value the number of cells of which is the greatest. In this case, in a case where the most frequent value is selected, an image showing a cell indicating the most frequent value is displayed. The analysis device 10 may display all the images showing the cell indicating the most frequent value at the same time, or may select a representative one to display it.

In a case where the user selects "Maximum value", the criterion selecting unit 405 adds a criterion to the image selection criterion CR1 so that an image indicating the maximum value is acquired from images having various feature values. The image indicating the maximum value is, for example, an image having a feature value with the greatest size of all of the images extracted as images having a correlation. The image is caused to be displayed.

In a case where the user selects "Minimum value", the criterion selecting unit 405 adds a criterion to the image selection criterion CR1 so that an image indicating the minimum value is acquired from images having various feature values. The image indicating the minimum value is, for example, an image having a feature value with the greatest size of all the images extracted as images having a correlation and is displayed.

The range of tolerance is also set on the screen UI2.

In a case where the user selects "up to second one" as the range of tolerance, the criterion selecting unit 405 adds, as the range of tolerance, values up to the second value from values of the type designated for the image selection criterion CR1. More specifically, in a case where the user selects the "Maximum value" as the type of value and selects "up to second one" as the range of tolerance, a criterion is added to the image selection criterion CR1 so that an image in which the image selection criterion CR1 includes a feature value of "from the maximum value to the second one" is acquired.

In a case where the user selects "±10" as the range of tolerance, the criterion selecting unit 405 adds, as the range of tolerance, a value±10 from values of type designated for the image selection criterion CR1. More specifically, in a case where the user selects the "Average value" as the type of value and selects "±10" as the range of tolerance, a criterion is added to the image selection criterion CR1 so that an image in which the image selection criterion CR1 includes a feature value of "±10 from the average value" is acquired.

In a case where the user selects "40%" as the range of tolerance, the criterion selecting unit 405 adds, as the range of tolerance, a value of 40% from a value of type designated for the image selection criterion CR1. More specifically, in a case where the user selects the "Average value" as the type of value and selects "40%" as the range of tolerance, a criterion is added to the image selection criterion CR1 so that an image in which the image selection criterion CR1 includes a feature value of "40% from the average value" is acquired.

Case where Feature Value is Selected in Step S120

With reference to FIG. 7, a description will be made of an example of the method for selecting a feature value A in a case where a feature value is selected as the image selection criterion CR1.

FIG. 7 is a diagram illustrating an example of a feature value in the case where the feature value is selected as the image selection criterion CR1.

As one example of a feature value supplied from the computing unit 100, a cell "101" and "100" serving as a feature value A are contained in a state of being associated with each other, as illustrated in FIG. 7. The node ND supplied from the computing unit 100 contains a cell "2" and "100" serving as a feature value A in a state of being associated with each other. The node ND supplied from the computing unit 100 contains a cell "23" and "98" serving as a feature value A in a state of being associated with each other. The node ND supplied from the computing unit 100 contains a cell "1300" and "97" serving as a feature value A in a state of being associated with each other. Note that, in this example, values indicating the feature value A are listed in descending order.

In a case where the "maximum value" is selected as a type of value concerning the image selection criterion CR1, the first image selecting unit 40 selects, from images having the feature value A, an image containing the cell "101", and the cell "2", these cells having the maximum values of the feature value.

Case where Measurement Target is Selected in Step S120

With reference to FIG. 8, a description will be made of an example of the method for selecting a cell image NP in a case where a feature value selected by a user is selected as the image selection criterion CR1 and a measurement target.

FIG. 8 is a diagram illustrating an example concerning feature values in a case where measurement targets are selected as image selection criteria CR1.

As illustrated in FIG. 8, the node ND supplied from the computing unit 100 contains a cell "101" serving as a feature value serving as a measurement target, "100" serving as a feature value A, and "100" serving as a feature value B in a state of being associated with each other. The node ND supplied from the computing unit 100 contains a cell "2" serving as a feature value serving as a measurement target, "100" serving as a feature value A, and "80" serving as a feature value B in a state of being associated with each other. The node ND supplied from the computing unit 100 contains a cell "23" serving as a feature value serving as a measurement target, "78" serving as a feature value A, and "98" serving as a feature value B in a state of being associated with each other. The node ND supplied from the computing unit 100 contains a cell "1300" serving as a feature value serving as a measurement target, "100" serving as a feature value A, and "75" serving as a feature value B in a state of being associated with each other. Note that, in this example, values obtained by adding values contained in the feature value A and values contained in the feature value B together are listed in descending order.

In a case where the "maximum value" is selected as a type of value of the image selection criterion CR1, the first image selecting unit 404 adds the feature value A and the feature value B together to calculate the added feature value. The first image selecting unit 404 selects an image containing the cell "101" having the greatest added feature value of all of the added feature values.

In other words, in a case where the node ND is selected and a type of value is designated, the range of values and the range of tolerance of values for the image selection criterion CR1 are determined on the basis of a result of addition of a plurality of feature values corresponding to the node ND.

Case where Image Selection Criterion CR1 is Selected on the Basis of Standard Deviation of Node ND Next, a criterion for selecting an image selection criterion CR1 on the basis of standard deviation of a node ND will be described with reference to FIG. 9.

Figure 9:
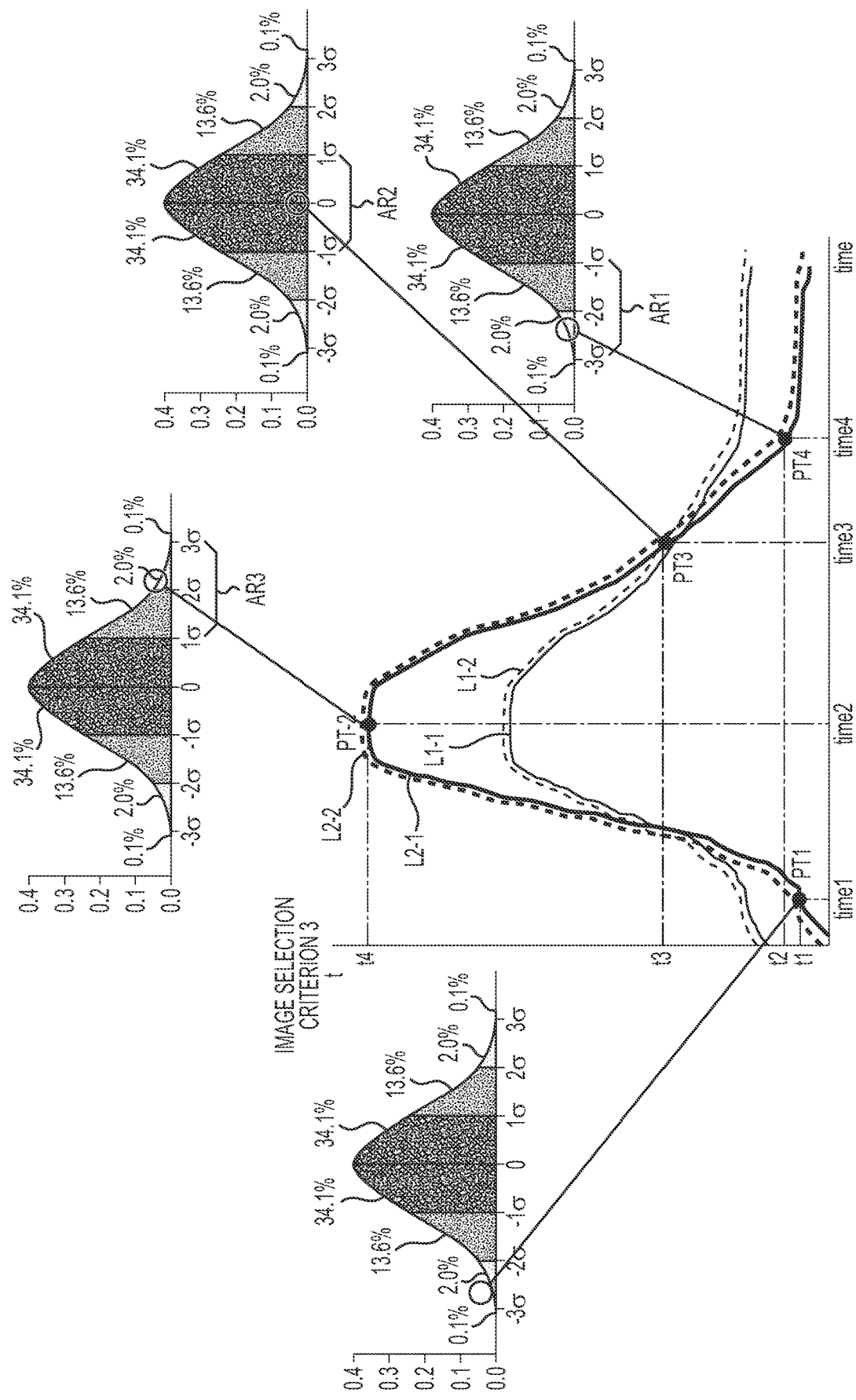
FIG. 9 is a diagram illustrating an example of a graph showing temporal change in feature values of imaged cells.

FIG. 9 is a diagram illustrating an example of a graph showing temporal change in values of feature values of captured cells.

The graph shown in FIG. 9 is a graph in which the vertical axis represents values t of feature value and the horizontal axis represents time. The broken line L1-1 and the dashed line L1-2 are lines based on the average values t1-1 and t1-2 of values of the feature value 1 and the feature value 2, respectively. The average of feature values t that the broken line L1-1 indicates is, for example, an average of feature values t in a plurality of cell images acquired at a time 1 in response to a stimulus. On the other hand, the broken line L2-1 and the line L2-2 are lines indicating values used to select a representative image from among images stained with a protein A forming the feature value 1 and images stained with a protein B forming the feature value 2, respectively. For example, at the time 1, a representative image indicating a value PT1 less than the average is selected from the histogram concerning the value t1-1 of the feature value 1. Thus, the point PT1 on the selected L2-1 is obtained as a result of selection of a cell image having a value (value obtained by subtracting 3$a$ from the average) of a feature value three times or more smaller than the standard deviation from the average, from the plurality of acquired cell images. The selected cell image may be a representative image having a value of the feature value, or may be one image. In addition, the broken line L1-1 and the dashed line L1-2 similarly change as time changes, and hence, indicate that the feature value 1 and the feature value 2 have high correlation. In this Example, the broken line L1-1 and the dashed line L1-2 represent, for example, information on change in the feature values of ND1-4 and ND2-8 that form the ED3 in a case where the ED3 is selected in FIG. 4. In the present embodiment, since the changes in the feature values are equal between ND1-4 and ND2-8, the broken line and the dashed line are equal. Of course, the change in the feature values may not be equal between ND1-4 and ND2-8. For example, while the size of the feature value of ND1-4 may change so as to decrease, the size of the feature value of ND2-8 may change so as to increase.

In a case where the value t of the feature value is a value PT4 that is less than the reference value t3, the criterion selecting unit 405 designates an image selection criterion CR1 so that an image, corresponding to an image captured at the same time and in a region AR1 in which a value of the feature value is less than the average, is selected. The reference value t3 may be the average of values of feature values for all times, or may be the median value or any value designated by a user. In a case where the value t of the feature value sits in a region similar to that of the reference value t3, the criterion selecting unit 405 designates an image selection criterion CR1 so that an image, corresponding to an image captured at the same time and in a region AR2 in which a value of the feature value is in the vicinity of the average, is selected. In a case where the value t of the feature value sits in a region greater than the reference value t3, the criterion selecting unit 405 designates an image selection criterion CR1 so that an image, corresponding to an image captured at the same time and in a region AR3 in which a value of a feature value is greater than the average, is selected. Note that, in a case where an image in a region AR in which a value of the feature value is greater than or less than the average is selected, the criterion selecting unit 405 may use a standard deviation designated by a user as a threshold value for selection.

More specifically, the image selection criterion CR1 designated at the point PT1 (time 1, t1) illustrated in FIG. 9 is designated on the basis of the value t1 of a feature value associated with an image of cells captured at the time 1. The image selection criterion CR1 includes the value t1 of a feature value less than the reference t3, and hence, is designated so that an image indicating a value less than the average in the distribution of values of the feature value 1 at the time 1 is selected.

Similarly, the image selection criterion CR1 designated at the point PT4 (time 4, t2) includes the value t2 of a feature value less than the reference t3, and hence, is designated so that an image indicating a value less than the average in the distribution of values of the feature value 1 at the time 4 is selected.

The image selection criterion CR1 designated at the point PT2 (time 2, t4) includes the value t4 of a feature value greater than the reference t3, and hence, is designated so that an image indicating a value greater than the average in the distribution of values of the feature value 1 at the time 2 is selected.

The image selection criterion CR1 designated at the point PT3 (time 3, t3) includes the value t3 of a feature value equal to the reference, and hence, is designated so that an image in the vicinity of the average value in the distribution of values of the feature value 1 at the time 3 is selected.

The criterion selecting unit 405 outputs the node ND to the display control unit 300 on the basis of the node ND acquired from the computing unit 100. The display control unit 300 causes the display unit 30 to display the node ND. The user operates the manipulation unit 40 to select the node ND displayed on the display unit 30. The operation detecting unit 500 detects the node ND selected by the user. The operation detecting unit 500 outputs the detected node ND to the criterion selecting unit 405. The criterion selecting unit 405 outputs the node ND detected by the operation detecting unit 500 to the first image selecting unit 404 as the image selection criterion CR1.

The first image selecting unit 404 acquires a captured image BP and the node ND from the computing unit 100. In addition, the first image selecting unit 404 acquires the image selection criterion CR1 outputted by the criterion selecting unit 405.

The first image selecting unit 404 acquires the first feature value selected by the feature value selecting unit 403. The first image selecting unit 404 acquires the image selection criterion CR1 from the criterion selecting unit 405. The first image selecting unit 404 selects, from captured images BP, an image that meets the first feature value and the image selection criterion CR1 as the cell image NP (step S160). Note that, in a case where the criterion selecting unit 405 does not select the image selection criterion CR1, the first image selecting unit 404 may select, from captured images BP, an image that meets the first feature value as the cell image NP. In other words, all of the captured images BP may be set as the captured image NP. The user performs selection as to whether the cell image NP selected by the first image selecting unit 404 is an image indicating a desired feature value (step S132). In a case where the user judges that the cell image NP is not appropriate for indicating the feature value or that the number of cell images NP selected is small and is not appropriate for comparison, the user selects NO. In this case, the analysis device 10 may redo the processes from the calculation of a feature value in step 114, or may redo the processes from the extraction of a correlation in step S116 (NO in step S132). In a case where the user judges that the cell image NP is appropriate for indicating the correlation, the user selects YES. The analysis device 10 terminates the process (YES in step S130).

The first image selecting unit 404 outputs the selected cell image NP to the display control unit 300.

The display control unit 300 causes the display unit 30 to display the captured image BP that meets the image selection criterion CR1 acquired from the first image selecting unit 404.

As described above, the analysis device 10 includes the feature value selecting unit 403, the first image selecting unit 404, and the criterion selecting unit 405. The feature value selecting unit 403 selects a first feature value from a plurality of nodes ND acquired from the computing unit 100. The first image selecting unit 404 selects an image that corresponds to the first feature value selected by the feature value selecting unit 403, from the plurality of captured images BP as cell images NP. In other words, the analysis device 10 can select an image that corresponds to the first feature value selected by a user, from among the captured images BP. In addition, in a case where a user cannot select a desired image, the analysis device 10 may redo the multi-scale analysis. With the configuration described above, it is possible to reduce efforts of the user who selects the cell image NP having a feature value desired by the user from a large number of images in which the cells are captured. Typically, the number of captured images containing fixed cells therein is large. Hence, it takes lots of efforts for a user to manually select cell images NP that meet applications desired by the user, and such selection is difficult. The cell observation system 1 is particularly effective in selecting a cell image that satisfactorily indicates a certain feature, from captured images of fixed cells. Note that, in the description above, a user operates the manipulation unit 40 and selects the first feature value on the screen UI to select an image selection criterion CR1. However, it may be possible to use a predetermined image selection criterion CR1. Note that the captured images BP selected by the analysis device 10 are not limited to the images captured by the microscopic device 20, and may be, for example, images stored in advance in a cell-image storage unit 203 of the storage unit 200, or images stored in advance in an external storage device (not illustrated).

In addition, in the description above, the display unit 30 is caused to display images selected by the first image selecting unit 404. However, causing the display unit 30 to display is not essential. A user may use another method to cause an image selected by the first image selecting unit 404 to be displayed.

Functional Configuration of Analysis Device 10a According to Second Embodiment

The method for selecting a cell image NP on the basis of an image selection criterion CR1 has been described.

Next, a first image selecting unit 404a according to the second embodiment of the present invention will be described. Note that the same reference characters are attached to the same configurations and operations as those in the first embodiment, and the description thereof will be omitted.

An analysis device 10a includes the first image selecting unit 404a.

The first image selecting unit 404a acquires a plurality of captured images BP acquired by the cell-image acquiring unit 101, from the computing unit 100. The first image selecting unit 404a selects a cell image NP that corresponds to the first feature value selected by the feature value selecting unit 403. A user selects a desired cell image from cell images NP. The first image selecting unit 404a selects a cell image N P selected by a user, as a re-selected image SP. The re-selected image SP includes images from a re-selected image SP1 to a re-selected image SPk. Here, the character "k" in the re-selected image SPk represents an integer not less than zero and not greater than n. Thus, in the present embodiment, the number of re-selected images SP is less than the number of cell image NP. The first image selecting unit 404a outputs the selected re-selected image SP to the display control unit 300. The display control unit 300 acquires the re-selected image SP from the first image selecting unit 404a to cause the display unit 30 to display it. The display unit 30 displays the re-selected image SP.

Example of Operation Performed by Analysis Device 10a According to Second Embodiment Next, a description will be made of an example of operation in a case where the analysis device 10a selects a re-selected image SP from captured images BP, with reference to FIGS. 10 and 11.

Figure 10:
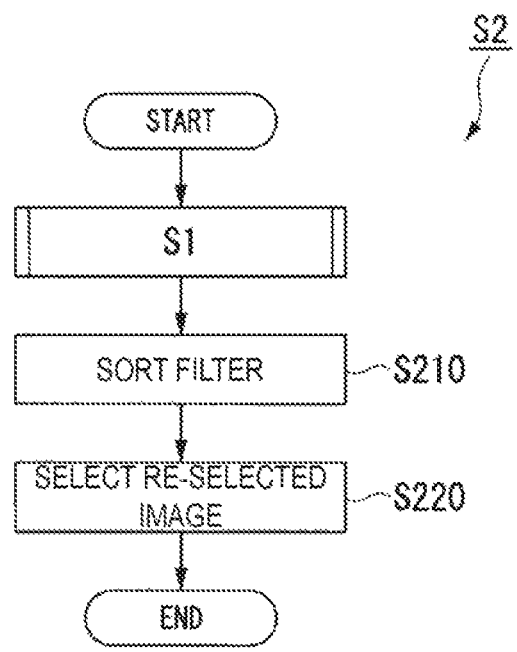
FIG. 10 is a flowchart illustrating an example of an operation performed by an analysis device according to a second embodiment.

FIG. 10 is a flowchart S2 illustrating an example of an operation performed by the analysis device 10a according to the second embodiment.

The first image selecting unit 404a included in the analysis device 10a performs the process in the flowchart S1 described in the first embodiment and selects cell images NP. The first image selecting unit 404a sorts and filters the selected cell images NP on the basis of feature values and outputs them to display control unit 300 (step S210). The display control unit 300 causes the display unit 30 to display the cell images NP acquired from the display control unit 300. A user selects a desired cell image from the cell images NP displayed on the display unit 30. The first image selecting unit 404a selects a re-selected image SP from the cell images NP on the basis of user operation (step S220).

Figure 11:
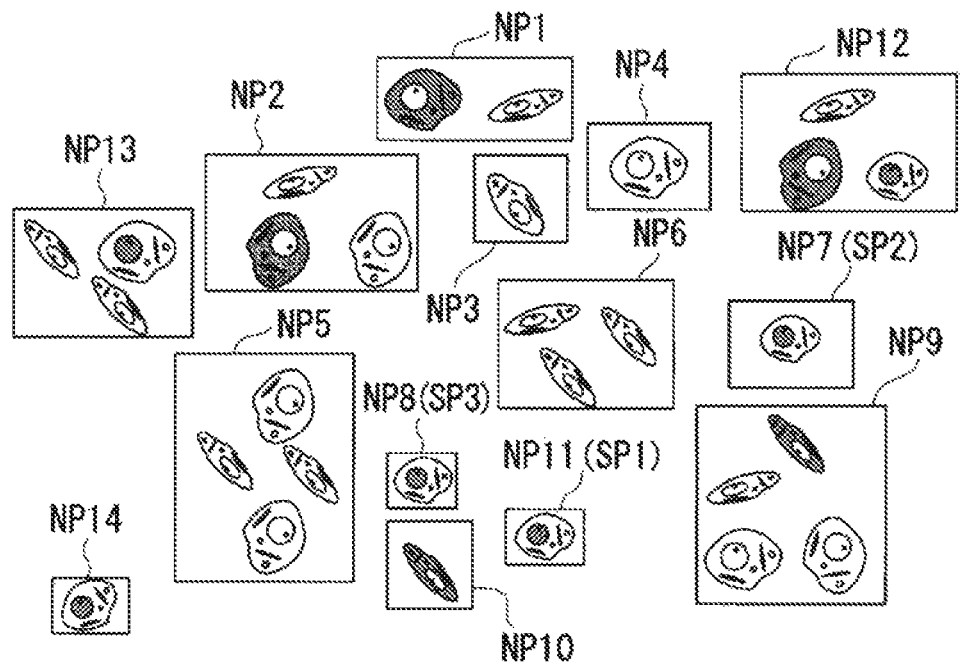
FIG. 11 is a diagram illustrating examples of re-selected images selected by a first image selecting unit.

FIG. 11 is a diagram illustrating examples of re-selected images SP selected by the first image selecting unit 404a.

The cell images NP include images from a cell image NP1 to a cell image NP14. A user selects a re-selected image SP from the cell images NP. More specifically, the user selects the cell image NP11 as a re-selected image SP1. The user selects the cell image NP7 as the re-selected image SP2. The user selects the cell image NP8 as the re-selected image SP3.

As described above, the analysis device 10a according to the second embodiment includes the first image selecting unit 404a. The first image selecting unit 404a selects, on the basis of an instruction made by a user, a re-selected image SP corresponding to the instruction, from the cell images NP. In other words, the analysis device 10a and the cell images NP can select a captured re-selected image SP. A user can additionally select, as a re-selected image SP, a desired image from the cell images NP that meet an image selection criterion CR1 from among captured images BP. With the configuration described above, the analysis device 10a allows the user to select, as a re-selected image SP, an image desired by the user from among the cell images NP selected by the first image selecting unit 404a. After the analysis device 10a has selected the cell images NP from the captured images BP, a user can easily select a desired image.

Functional Configuration of Analysis Device 10b According to Third Embodiment

The method for selecting a re-selected image SP from the cell images NP on the basis of an instruction made by a user has been described.

Next, a first image selecting unit 404b according to the third embodiment of the present invention will be described. Note that the same reference characters are attached to the same configurations and operations as those in the first embodiment and the second embodiment, and the description thereof will be omitted.

An analysis device 10b includes a cell-image selecting unit 400b. The cell-image selecting unit 400b includes the first image selecting unit 404b.

The first image selecting unit 404b selects cell images NP each corresponding to an image selection criterion CR1. The first image selecting unit 404b selects a re-selected image SP from the cell images NP on the basis of operation performed by a user. The first image selecting unit 404b selects, from a plurality of captured images BP, images each having a shape that has high correlation with the cell images NP and the re-selected image SP, as machine learning images TP that each correspond to the image selection criterion CR and the re-selected image SP. In other words, the cell-image selecting unit 400b selects images from the plurality of images through machine learning on the basis of the re-selected image SP. The machine learning images TP include images from a machine learning image TP1 to a machine learning image TPm. Here, the character "m" in the machine learning image TPm represents an integer not less than one and not greater than n.

The first image selecting unit 404b outputs the machine learning image TP to the display control unit 300. The display control unit 300 acquires the machine learning image TP from the first image selecting unit 404b to cause the display unit 30 to display it. The display unit 30 displays the machine learning image TP.

Example of Operation Performed by Analysis Device 10b According to Third Embodiment Next, a description will be made of an example of an operation in a case where the analysis device 10b selects a machine learning image TP from captured images BP, with reference to FIGS. 12 and 13.

Figure 12:
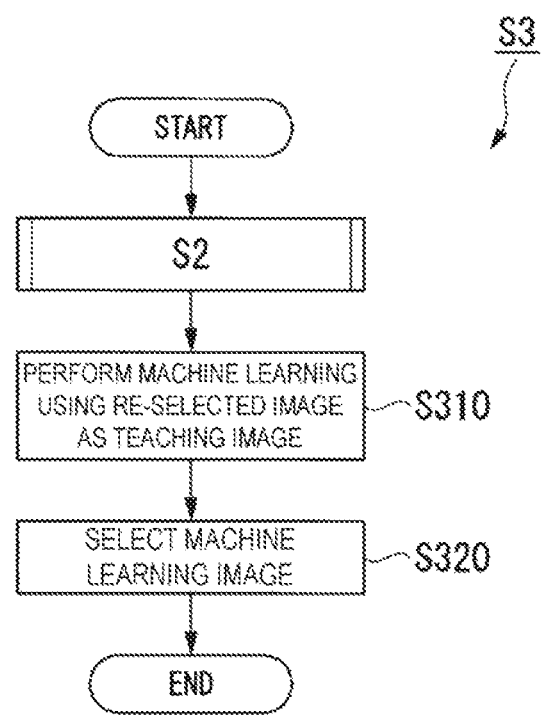
FIG. 12 is a flowchart illustrating an example of an operation performed by an analysis device according to a third embodiment.

FIG. 12 is a flowchart S3 illustrating an example of an operation performed by the analysis device 10b according to the third embodiment.

The first image selecting unit 404b included in the analysis device 10b performs the process in the flowchart S2 described in the second embodiment to select a re-selected image SP. The first image selecting unit 404b performs machine learning using the re-selected image SP as a training image (step S310). The first image selecting unit 404b selects the machine learning image TP from captured images BP on the basis of results of machine learning performed using the re-selected image SP as the training image and an image selection criterion CR1 (step S320).

Figure 13:
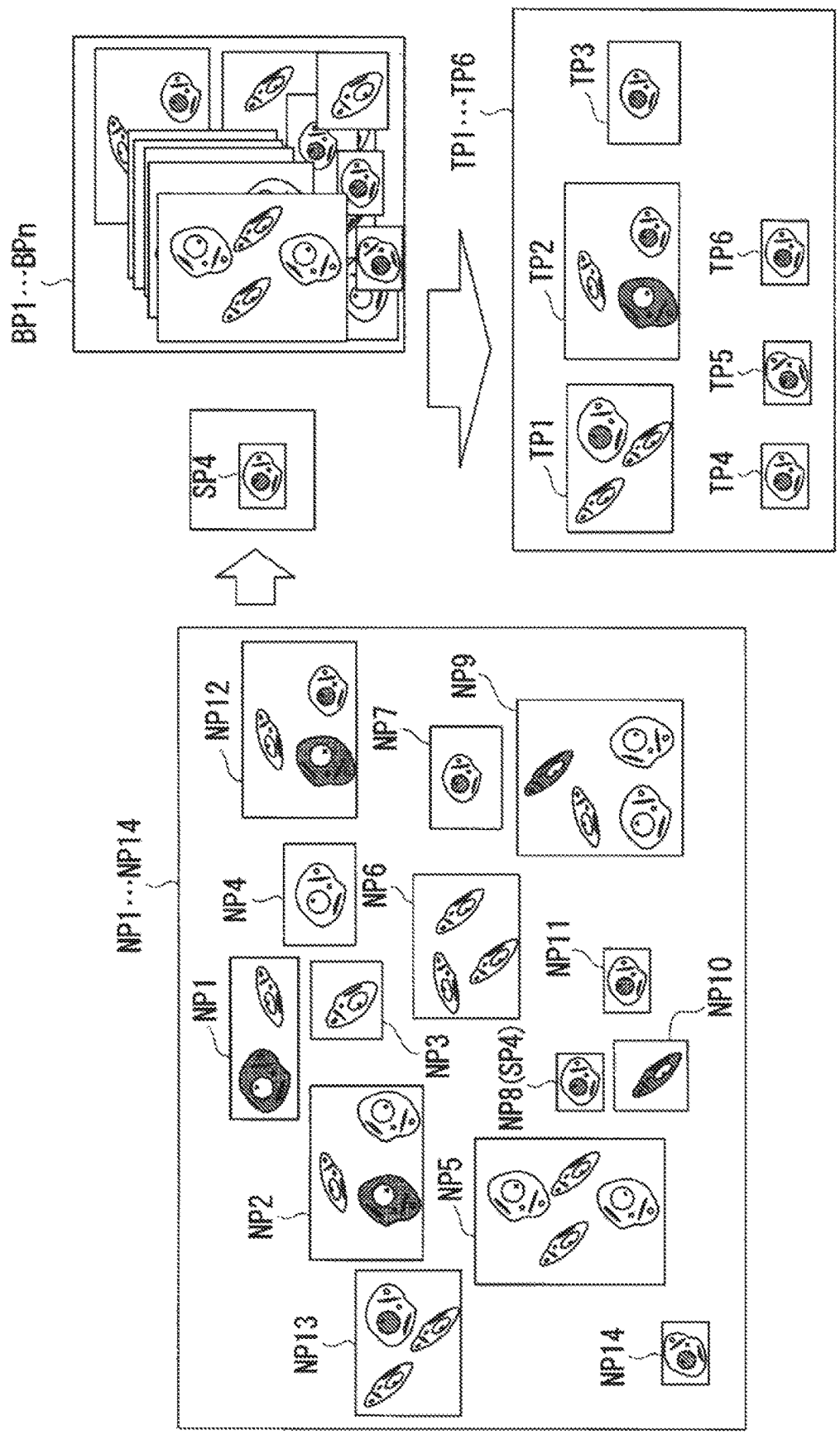
FIG. 13 is a diagram illustrating examples of captured images, re-selected images, and machine learning images.

FIG. 13 is a diagram illustrating examples of cell images NP, re-selected images SP, and machine learning images TP. The cell images NP include images from a cell image NP1 to a cell image NP14. A user selects the cell image NP8 of the cell images NP as the re-selected image SP4. The first image selecting unit 404b performs machine learning using the re-selected image SP4 as a training image. The first image selecting unit 404b selects the machine learning image TP from captured images BP on the basis of results of machine learning performed using the re-selected image SP4 and an image selection criterion CR1. The machine learning images TP include images from a machine learning image TP1 to a machine learning image TP6. Note that it is only necessary that the machine learning image TP selected by the first image selecting unit 404b contains an image that resembles the training image (has a high correlation), and it may be possible to select, as the machine learning image TP, an image containing a cell that does not resemble a cell included in the training image as illustrated in the machine learning image TP1 and the machine learning image TP2.

As described above, the first image selecting unit 404b included in the analysis device 10b according to the third embodiment performs machine learning using the re-selected image SP selected by a user as a training image. A user can select a re-selected image SP as the training image that is an image of a cell indicating a desired correlation. The first image selecting unit 404b selects the machine learning image TP from captured images BP on the basis of results of machine learning performed using the re-selected image SP as the training image and an image selection criterion CR1. The machine learning image TP represents an image that corresponds to a cell image NP that meets the image selection criterion CR1 and also corresponds to a re-selected image SP that a user selects from the cell images NP. The configuration described above allows the user to select a desired image, without efforts, as the training image from a large number of images in which the cells are captured. In addition, the first image selecting unit 404b selects the machine learning image TP from captured images BP on the basis of results of machine learning performed using the desired image selected by the user as the training image and the image selection criterion CR1 selected by the user. In other words, the first image selecting unit 404b can select not only the image selection criterion CR1 but also the machine learning image TP that corresponds to the re-selected image SP. The analysis device 10b can select an image appropriate for an application for publication of a research paper, an application for checking temporal change of cells, and an application for removing, from the captured images BP, images containing abnormal values and captured dust, each of which is an application that a user desires. Thus, the user can easily obtain images of cells more appropriate for desired applications, from among a large number of captured images BP. Note that, in the present embodiment, re-selected images SP selected by a user from cell images NP are used so that a machine learning TP is extracted from cell images BP. However, the present embodiment is not limited to this. For example, it may be possible to use a machine learning TP to further extract an image of cells from captured images BP through machine learning. In addition, in a case where the number of images obtained through machine learning is small, it may be possible to determine that a correlation is not formed on the basis of images desired by a user and review nodes and edges again.

Functional Configuration of Analysis Device 10c According to Fourth Embodiment

The method for selecting, from captured images BP, a machine learning image TP on the basis of an image selection criterion CR1 and results of machine learning using a re-selected image SP as a training image has been described.

Next, a second image selecting unit 406 according to a fourth embodiment of the present invention will be described with reference to FIG. 14.

Figure 14:
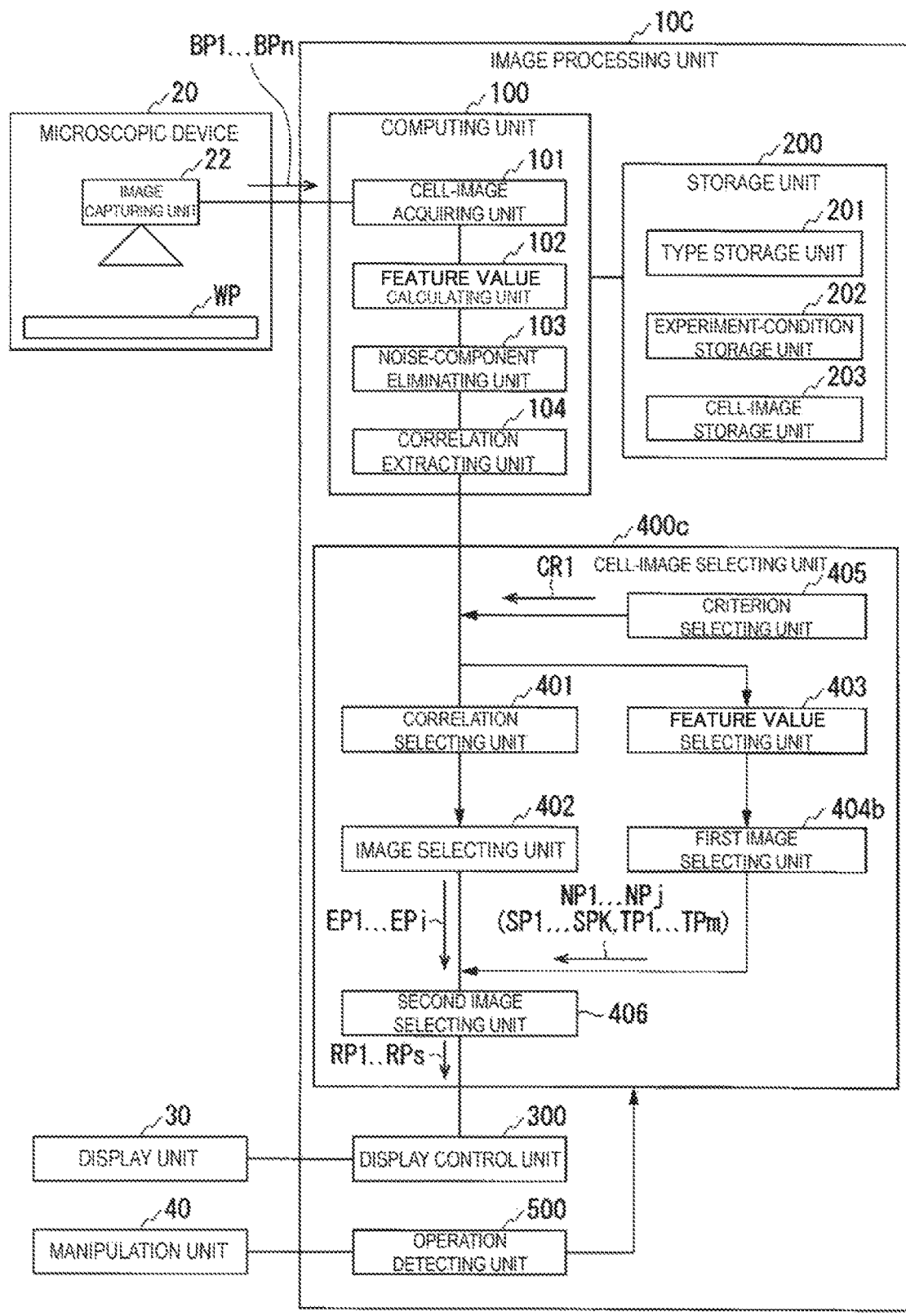
FIG. 14 is a diagram illustrating an example of a functional configuration of an analysis device according to a fourth embodiment.

FIG. 14 is a diagram illustrating an example of a functional configuration of an analysis device 10c according to the fourth embodiment. Note that the same reference characters are attached to the same configurations and operations as those in the first embodiment, the second embodiment, and the third embodiment, and the description thereof will be omitted.

The analysis device 10c further includes the second image selecting unit 406.

The second image selecting unit 406 acquires the cell images NP, the re-selected images SP, or the machine learning images TP, selected by the first image selecting unit 404b, as a plurality of captured images BP that meet the image selection criterion CR1. The second image selecting unit 406 outputs the plurality of captured images BP that meet the image selection criterion CR1 to the display control unit 300. In addition, the second image selecting unit 406 acquires operation of a user from the operation detecting unit 500.

The display control unit 300 causes the display unit 30 to display, as displayed images, the plurality of captured images BP that meet the image selection criterion CR1 for each of the image selection criteria CR.

The second image selecting unit 406 selects, as a representative image selected by the user, a representative image RP from the plurality of captured images BP displayed by the display control unit 300 on the basis of an instruction made by the user and a second criterion CR2 that is a criterion different from the image selection criterion. The representative image RP includes images from a representative image RP1 to a representative image RPs. Here, the character "s" in the representative image RPs represents an integer not less than one and not greater than n. Note that, in the present embodiment, the cell image NP, the re-selected image SP, and the machine learning image TP may be different images from each other, or two of them may be the same images, and the same images may be selected. Of course, the cell image NP, the re-selected image SP, and the machine learning image TP may be the same image, and the same image may be selected. Note that the display control unit 300 may cause the display unit 30 to display images captured at different magnifications and corresponding to the selected representative image RP.

Example of Operation Performed by Analysis Device 10c According to Fourth Embodiment Next, a description will be made of an example of operation in a case where the analysis device 10c selects a machine learning image RP, with reference to FIG. 15 to FIG. 18.

Figure 15:
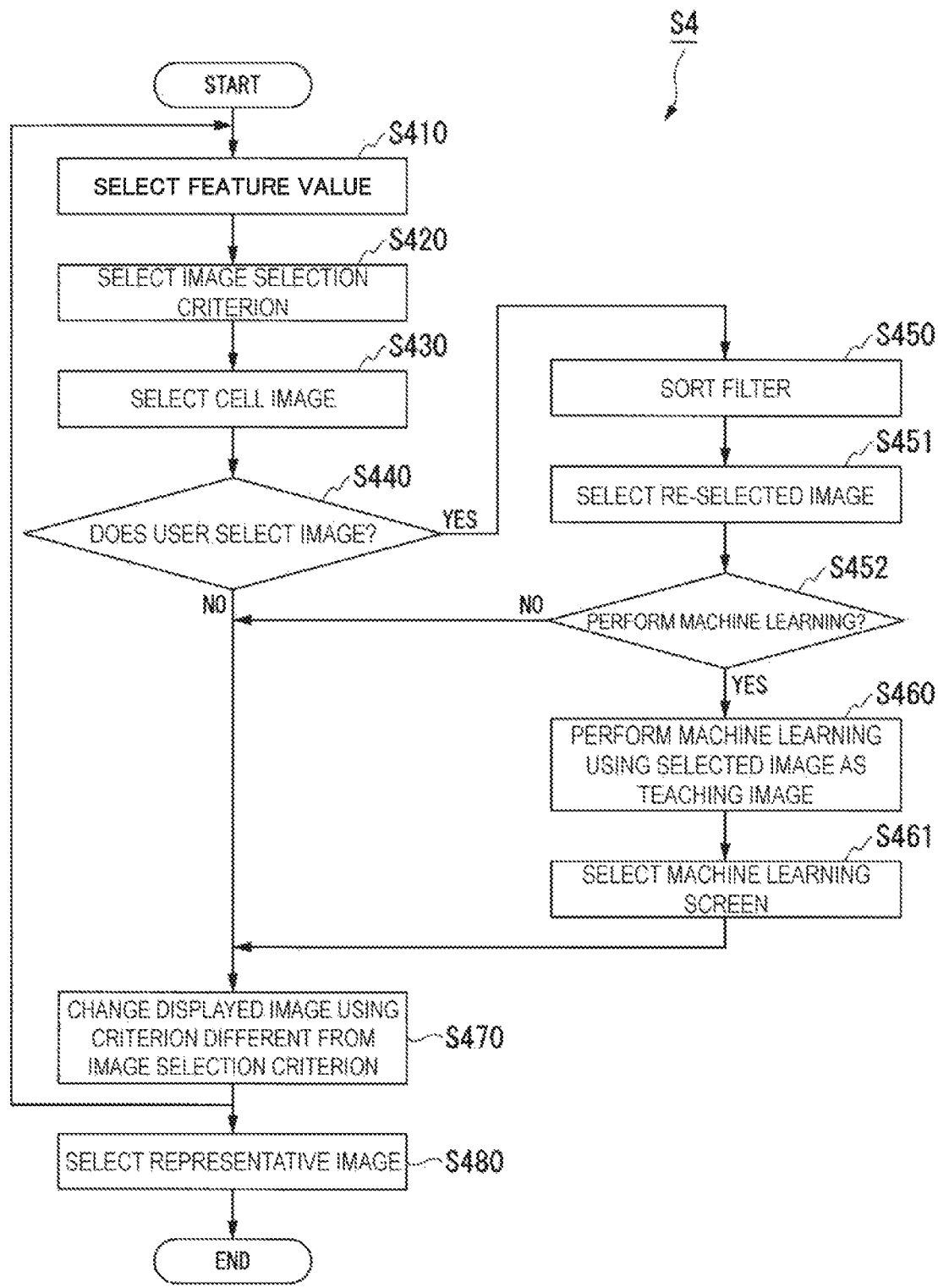
FIG. 15 is a flowchart illustrating an example of an operation performed by an analysis device according to the fourth embodiment.

FIG. 15 is a flowchart S4 illustrating an example of an operation performed by the analysis device 10c according to the fourth embodiment.

A cell-image selecting unit 400c included in the analysis device 10c acquires captured images BP from the computing unit 100, a plurality of types of feature values obtained through the application of multi-scale analysis to the captured images BP, and a plurality of correlations between feature values. A user designates a feature value as a criterion for an image selected by the analysis device 10c. The feature value selecting unit 403 included in the cell-image selecting unit 400c selects a feature value on the basis of an instruction made by the user (step S410). The criterion selecting unit 405 sets the feature value selected by the user, as one image selection criterion CR. In addition, the criterion selecting unit 405 further outputs a plurality of criteria to the display control unit 300. The display control unit 300 causes the display unit 30 to display the plurality of criteria. The user selects a condition for a desired image and a condition for a feature value from the plurality of criteria displayed on the display unit 30. The criterion selecting unit 405 sets a condition for the selected feature value as one image selection criterion CR1 (step S420). The first image selecting unit 404b selects a cell image NP corresponding to the image selection criterion CR from among the plurality of captured images BP on the basis of the image selection criterion CR selected by the criterion selecting unit 405 (step S430). The analysis device 10c receives whether the user selects an image (step S440). In a case where the user selects "Select an image" (YES in step S440), the analysis device 10c sorts and filters the selected cell images NP on the basis of feature values and outputs them to the display control unit 300 (step S450). The display control unit 300 causes the display unit 30 to display the cell images NP acquired from the display control unit 300. The user selects a desired image from the cell images NP displayed on the display unit 30. The analysis device 10c selects a re-selected image SP from the cell images NP on the basis of operation performed by the user (step S451). The analysis device 10c receives whether machine learning is performed (step S452). In a case where the user selects "Perform machine learning" (YES in step S452), the first image selecting unit 404b included in the analysis device 10c performs machine learning using the re-selected image SP selected in step S451 as a training image (step S460). The first image selecting unit 404b selects a machine learning image TP from the captured images BP on the basis of results of machine learning performed in step S460 and the image selection criterion CR1. The first image selecting unit 404b outputs the selected machine learning image TP to the second image selecting unit 406 (step S461).

In a case where the user selects "Not select any image" (NO in step S440), the first image selecting unit 404b outputs the selected cell image NP to the second image selecting unit 406.

In a case where the user selects "Not perform machine learning" (NO in step S452), the first image selecting unit 404b outputs the selected re-selected image SP to the second image selecting unit 406.

The second image selecting unit 406 changes images (hereinafter, referred to as images of a plurality of cells that meet the image selection criterion CR1) that are to be displayed and acquired from the first image selecting unit 404b, using a criterion (hereinafter, referred to as a second criterion CR2) that is determined on the basis of an instruction made by the user and is different from the image selection criterion CR1. The second image selecting unit 406 outputs the changed images to be displayed to the display control unit 300. The display control unit 300 causes the display unit 30 to display the changed images (step S470). The user designates a representative image RP from the images displayed on the display unit 30. The second image selecting unit 406 selects a representative image RP on the basis of designation made by the user (step S480). In a case where the images displayed in step S470 do not contain cell images desired by the user, the analysis device 10c may redo the processes from the process performed by the feature value calculating unit 102 or the process performed by the correlation extracting unit 104.

Figure 16:
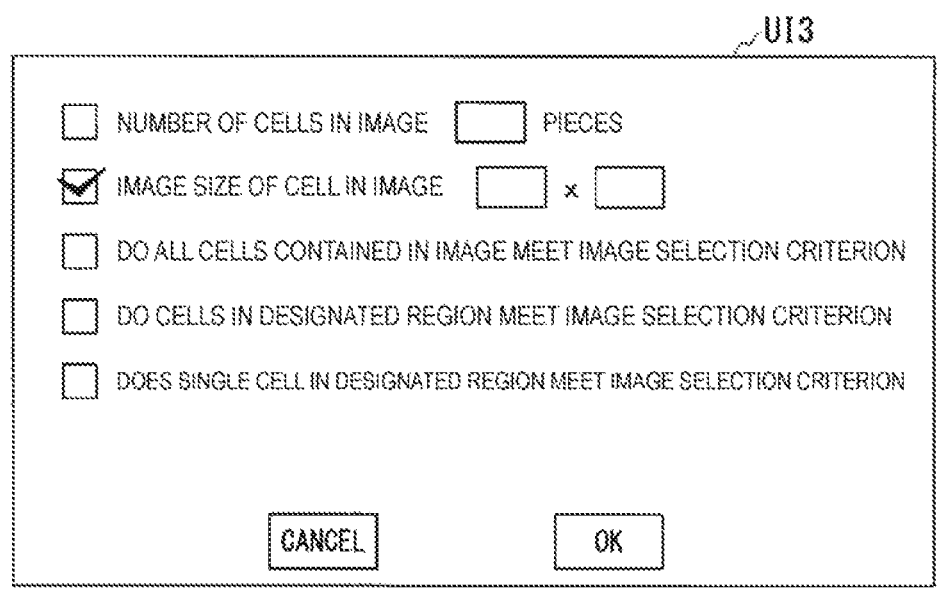
FIG. 16 is a diagram illustrating an example of a screen for selecting second criteria that is different from an image selection criterion.

FIG. 16 is a diagram illustrating an example of a screen U13 for selecting the second criteria CR2 that is different from the image selection criterion CR1.

The screen U13 is one example of a screen for designating "Number of cells in an image", "Image size of a cell in an image", "Do all the cells contained in the image meet an image selection criterion", "Do cells in the designated region meet an image selection criterion", and "Does a single cell in the designated region meet an image selection criterion". Note that, in a case where the second criterion CR2 is not selected in the screen UI3, the second image selecting unit 406 selects a representative image RP corresponding to an instruction made by a user from among a plurality of display images that the display control unit 300 causes to be displayed, on the basis of the instruction made by the user and acquired from the operation detecting unit 500.

In a case where the user selects "Number of cells in an image" and designates the number of cells, the second image selecting unit 406 adds the number of cells in the image to the second criterion CR2. The second image selecting unit 406 selects, as the representative image RP, an image that contains cells the number of which is designated by the user, from among the plurality of captured images BP that meet the image selection criterion CR1 on the basis of the second criterion CR2.

In a case where the user selects "Image size of a cell in an image" and designates the size of the image, the second image selecting unit 406 adds the image size of the cell contained in the image to the second criterion CR2. The second image selecting unit 406 selects, as the representative image RP, an image that contains cells the image size of which is designated by the user, from among the plurality of captured images BP that meet the image selection criterion CR1 on the basis of the second criterion CR2.

In a case where the user selects "Do all the cells contained in the image meet an image selection criterion", the second image selecting unit 406 adds, to the second criterion CR2, the criterion that all the cells contained in the image meet the image selection criterion CR1. The second image selecting unit 406 selects, as the representative image RP, an image in which all the cells contained in the captured image meet the image selection criterion CR1, from among the plurality of captured images BP that meet the image selection criterion CR1 on the basis of the second criterion CR2.

In a case where the user selects "Do cells in the designated region meet an image selection criterion", the second image selecting unit 406 adds, to the second image selection criterion CR2, the criterion that cells in the Region Of Interest (ROI) designated by the user meet the image selection criterion CR1. The second image selecting unit 406 selects, as the representative image RP, an image in which all the cells in the ROI designated by the user meet the image selection criterion CR1, from among the plurality of captured images BP that meet the image selection criterion CR1 on the basis of the second image selection criterion CR2.

In a case where the user selects "Does a single cell in the designated region meet an image selection criterion", the second image selecting unit 406 adds, to the second image selection criterion CR2, the criterion that a single cell in the ROI designated by the user meets the image selection criterion CR1. The second image selecting unit 406 selects, as the representative image RP, an image in which a single cell in the ROI designated by the user meets the image selection criterion CR1, from among the plurality of captured images BP that meet the image selection criterion CR1 on the basis of the second image selection criterion CR2.

Figure 17:
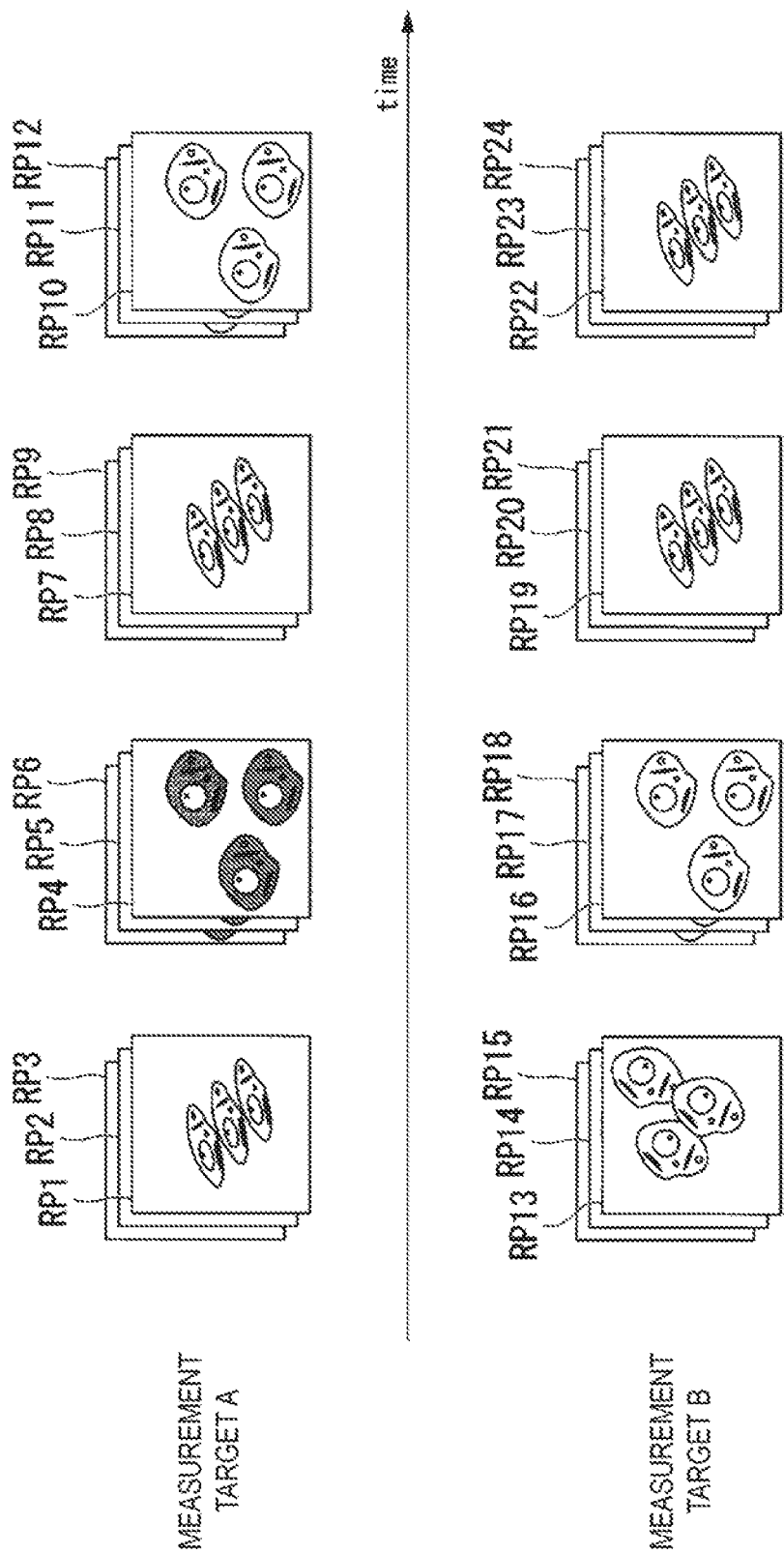
FIG. 17 is a diagram illustrating examples of representative images displayed on a display unit.

FIG. 17 is a diagram illustrating examples of representative images RP displayed on a display unit 30.

In these example, the representative images RP include images from a representative image RP1 to a representative image RP24.

The representative image RP1 to the representative image RP3 are images of cells captured at the same timing. The representative image RP4 to the representative image RP6, the representative image RP7 to the representative image RP9, the representative image RP10 to the representative image RP12, the representative image RP13 to the representative image RP15, the representative image RP16 to the representative image RP18, the representative image RP19 to the representative image RP21, and the representative image RP22 to the representative image RP24 are images of cells each captured at the same timing.

These representative images RP are displayed as display images on the display unit 30 for each image selection criterion CR1 in order of captured timing. More specifically, they are representative images RP for which a measurement target A and a measurement target B are designated as image selection criteria CR1.

Figure 18:
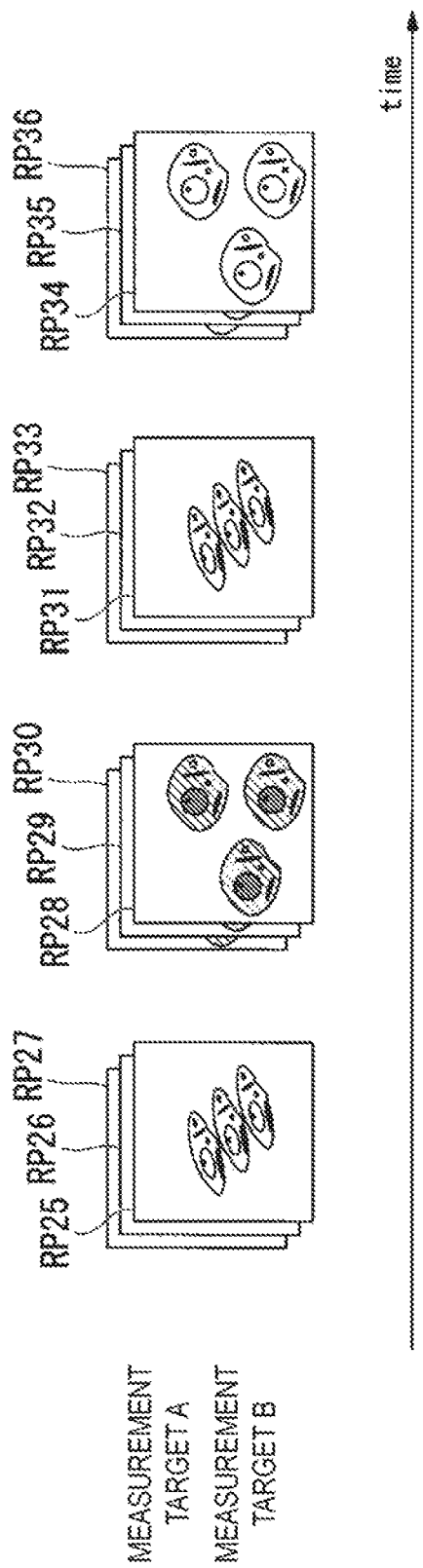
FIG. 18 is a diagram illustrating examples of representative images of cells that have been stained with a plurality of colors and are displayed on a display unit.

FIG. 18 is a diagram illustrating examples of representative images RP of cells that have been stained with a plurality of colors and are displayed on the display unit 30.

In these examples, the representative images RP include images from a representative image RP25 to a representative image RP36.

The representative image RP25 to the representative image RP27 are images of cells captured at the same timing. Similarly, the representative image RP28 to the representative image RP30, the representative image RP31 to the representative image RP33, and the representative image RP34 to the representative image RP36 are images of cells captured each at the same timing.

Figure 21:
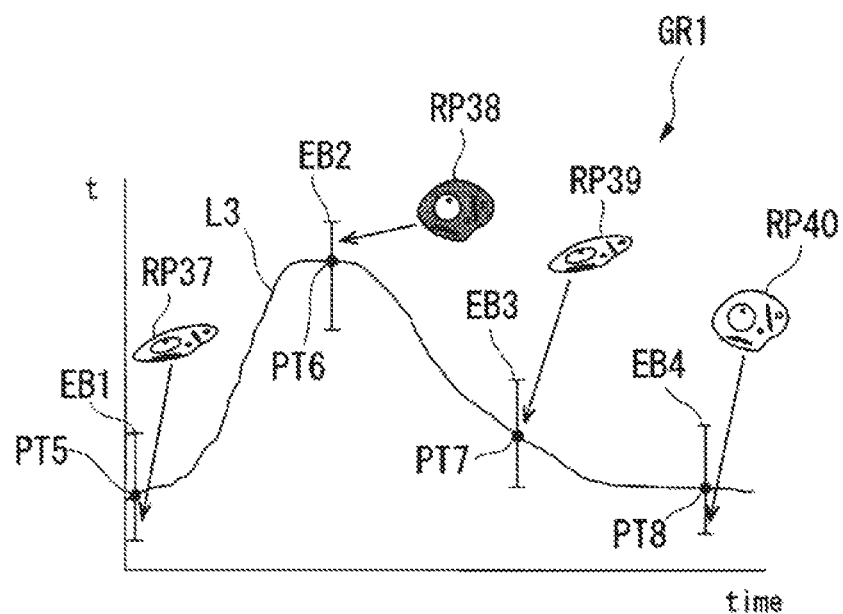
FIG. 21 is a diagram illustrating an example of a graph generated by a graph generating unit.

These representative images RP are displayed as display images on the display unit 30 for each image selection criterion CR1 in order of captured timing. In addition, the images of cells that have been stained with a plurality of colors are displayed so as to be overlapped for each of the colors. More specifically, the representative image RP28 to the representative image RP30 are displayed such that the representative image RP4 to the representative image RP6, the representative image RP16, and the representative image RP18 illustrated in FIG. 21 are overlapped.

As described above, the second image selecting unit 406 included in the analysis device 10c according to the fourth embodiment outputs the plurality of captured images BP that meet the image selection criterion CR1 to the display control unit 300. In addition, the second image selecting unit 406 selects the representative image RP from among the plurality of captured images BP that meet the image selection criterion CR on the basis of the second image selection criterion CR2 that is different from the image selection criterion CR1. In other words, the second image selecting unit 406 selects images having the shapes close to each other between the plurality of captured images BP meeting the image selection criterion CR1 and the representative image RP, from among the plurality of captured images BP. The second image selecting unit 406 outputs the selected representative image RP to the display control unit 300. The display control unit 300 causes the display unit 30 to display the acquired representative image RP. With the configuration described above, the analysis device 10c can cause images to be displayed on the basis of conditions designated by a user. In addition, this configuration allows a user to select images displayed. The user can select an image according to applications, from images of the captured images BP that meet the image selection criterion CR1 and the second image selection criterion CR2. In addition, in a case where the selected image does not contain an image indicating a correlation or feature value desired by a user, the cell observation system 1c can redo the multi-scale analysis. This allows the user to select an image that satisfactorily indicates a predetermined correlation or feature value, as the representative image RP. Note that, in the present embodiment, an image that meets the image selection criterion CR1 is used. However, it may be possible to extract an image of a reference that meets at least one of the second image selection criteria CR2, from the captured images BP.

Functional Configuration of Analysis Device 10d According to Fifth Embodiment

The description has been made of the method in which the analysis device 10c selects a representative image RP from captured images BP.

Next, a graph generating unit 407 according to a fifth embodiment of the present invention will be described with reference to FIG. 19.

Figure 19:
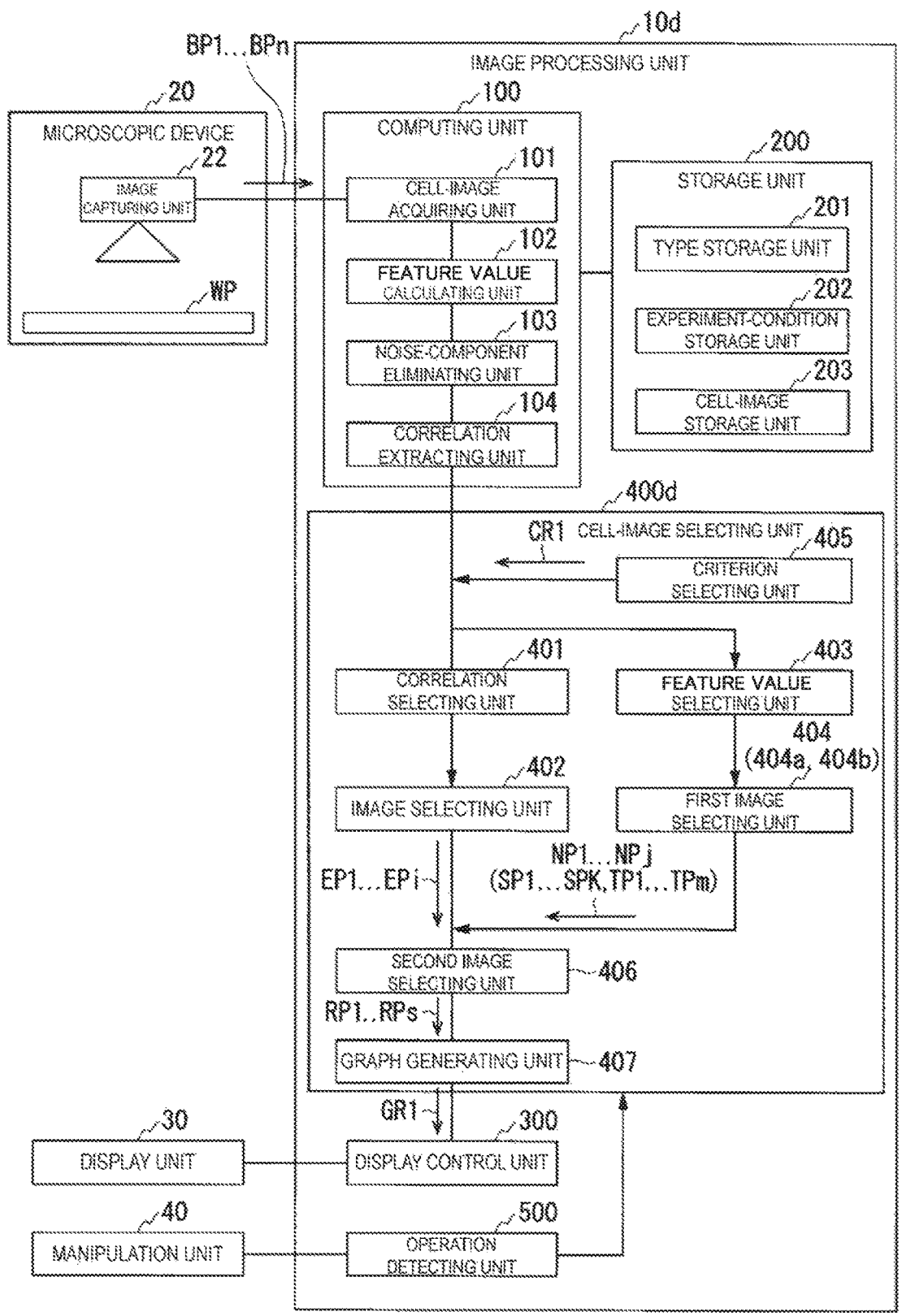
FIG. 19 is a diagram illustrating an example of a functional configuration of an analysis device according to a fifth embodiment.

FIG. 19 is a diagram illustrating an example of a functional configuration of an analysis device 10d according to the fifth embodiment. Note that the same reference characters are attached to the same configurations and operations as those in the first embodiment, the second embodiment, the third embodiment, and the fourth embodiment, and the description thereof will be omitted.

The analysis device 10d further includes the graph generating unit 407.

The graph generating unit 407 acquires a representative image RP selected by the second image selecting unit 406. The graph generating unit 407 generates a graph GR1 in which information on temporal change based on feature values, indicated in representative images RP captured as time elapses, is associated with the representative images RP. The information on temporal change represents information on a change in association with temporal change in feature values indicated in the representative image RP. In other words, the graph generating unit 407 calculates a change in feature values concerning constituent elements of cells captured in the representative image RP, on the basis of the representative image RP selected by the cell-image selecting unit 400, thereby generating a graph GR. The graph generating unit 407 outputs the generated graph GR1 to the display control unit 300. The display control unit 300 causes the display unit 30 to display the acquired graph GR1. Note that the graph generating unit 407 may generate a graph GR1 such that the information on temporal change, the representative image RP, and statistics of feature values are associated with each other.

Example of Operation Performed by Analysis Device 10d According to Fifth Embodiment Next, a description will be made of an example of operation in a case where the graph generating unit 407 included in the analysis device 10d generates the graph GR1, with reference to FIG. 20 to FIG. 21.

Figure 20:
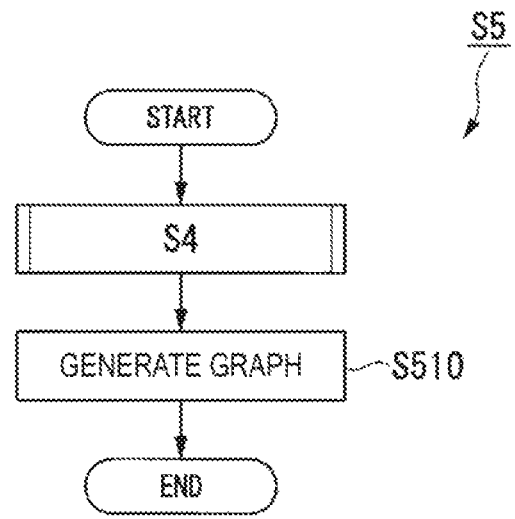
FIG. 20 is a flowchart illustrating an example of an operation performed by an analysis device according to the fifth embodiment.

FIG. 20 is a flowchart S5 illustrating an example of an operation performed by the analysis device 10d according to the fifth embodiment.

The analysis device 10d performs the process in the flowchart S4 described in the fourth embodiment and selects a representative image RP. The graph generating unit 407 included in the analysis device 10d generates the graph GR1 in which the representative images RP and the information on temporal change based on feature values, indicated in a plurality of captured images BP captured as time elapses and representative images RP, are associated with each other (step S510).

FIG. 21 is a diagram illustrating an example of the graph GR1 generated by the graph generating unit 407.

The graph GR1 is a graph in which the vertical axis represents feature values t and the horizontal axis represents time. The graph GR1 contains the broken line L3 based on feature values associated with representative images RP and temporal change in captured cells, indicated in a plurality of captured images BP captured as time elapses.

In addition, the graph GR1 contains a representative image RP37, a representative image RP38, a representative image RP39, and a representative image RP40. The graph GR indicates the broken line L3 and the representative image RP37 to the representative image RP40 such that they are associated with each other. More specifically, the representative image RP37 is an image captured at a time indicated as the point PT5. The representative image RP38 is an image captured at a time indicated as the point PT6. The representative image RP39 is an image captured at a time indicated as the point PT7. The representative image RP40 is an image captured at a time indicated as the point PT8.

In addition, in the graph GR1, error bars EB and representative images RP are associated with each other. The error bar EB represents information indicating statistics concerning feature values. More specifically, the error bar EB1 at the point PT5 and the feature value associated with the representative image RP37 are displayed so as to be associated with each other. The error bar EB2 at the point PT6 and the feature value associated with the representative image RP38 are displayed so as to be associated with each other. The error bar EB3 at the point PT7 and the feature value associated with the representative image RP39 are displayed so as to be associated with each other. The error bar EB4 at the point PT8 and the feature value associated with the representative image RP40 are displayed so as to be associated with each other.

More specifically, the representative image RP37 is selected as an image in which the standard deviation is on the negative side, from among feature values associated with the captured images BP captured at the same timing. Thus, the arrow pointing the lower portion in the error bar EB1 is drawn from the image of the representative image RP37. Similarly, the representative image RP40 is selected as an image in which the standard deviation is on the negative side, from among feature values associated with the captured images BP captured at the same timing. Thus, the arrow pointing the lower portion in the error bar EB4 is drawn from the image of the representative image RP40. The representative image RP38 is selected as an image in which the standard deviation is on the positive side, from among feature values associated with the captured images BP captured at the same timing. Thus, the arrow pointing the upper portion in the error bar EB2 is drawn from the image of the representative image RP38. The representative image RP39 is selected as an image in which the standard deviation is close to zero, from among feature values associated with the captured images BP captured at the same timing. Thus, the arrow pointing the center in the error bar EB3 is drawn from the image of the representative image RP37.

In graphs in which feature values of a predetermined constituent element of a cell change in response to a stimulus, in a case where cell images are acquired after a predetermined period of time elapses with respect to the stimulus, it is possible to display, as a graph, a representative image at a time after the predetermined period of time elapses. In the present embodiment, it is possible to classify a plurality of images captured after a predetermined period of time elapses on the basis of sizes of feature values in individual images. In the present embodiment, error bars corresponding to the sizes of feature values are indicated in the graph. By selecting the size of a feature value of an error bar, it is possible to display an image corresponding to the size of the feature value. In this case, the graph may or may not be changed on the basis of the size of the feature value in the selected image. For example, in a case where the graph is created using the average of sizes of feature values extracted from a plurality of images captured after the predetermined period of time elapses, it may be possible to change only the images resulting from the selection of the error bar while fixing the average value of the graph.

As described above, the graph generating unit 407 included in the analysis device 10d according to the fifth embodiment generates a graph GR in which the representative images RP and the information on temporal change of captured cells based on feature values, indicated in a plurality of captured images BP and representative images RP, are associated with each other. In addition, the graph generating unit 407 may associate the representative image RP with information indicating statistics of feature values to generate the graph GR1. With the configuration described above, the analysis device 10d can generate a graph that is associated with representative images RP selected by a user. For this reason, by selecting a representative image RP, a user can also obtain a graph GR that reflects features of the representative image RP. Thus, in a case where a user uses a representative image RP selected in a research paper and the like, the user operates the analysis device to select an image having a desired feature value as the representative image RP. Through this operation, the user can simultaneously obtain a graph GR1 associated with the selected representative image RP. This can reduce user efforts.

Note that, in the embodiment described above, an image is selected from among other captured images BP on the basis of a selected image. However, the embodiment is not limited to this. For example, in a case where the size of a feature value, for example, the magnitude of luminosity is high, it may be possible to change conditions for capturing images on the basis of the selected images. In other words, re-selection is performed for an image to be selected from captured images BP on the basis of the selected image. However, it may be possible to acquire an image that differs from an image contained in the population to which the selected image belongs. For the different image, the condition for capturing may be changed or may not be changed. In addition, for the different image, cells to be used may be changed. For example, a condition for staining cells may be changed. Of course, the type of the cell may be changed.

Note that the analysis device 10d may not include the computing unit 100. In this case, the analysis device 10d further includes an information acquiring unit (not illustrated).

The information acquiring unit acquires, from another device, a cell image BP in which a stimulated cell is captured, a feature value calculated from the cell image BP, and a correlation between constituent elements of a cell captured in the cell image BP, the correlation being calculated using the feature value, each of which is analyzed by the other device.

The analysis device 10d selects an image that meets the condition from among cell images BP on the basis of the correlation acquired by the information acquiring unit. Here, the condition represents an image selection criterion CR1 and a second image selection criterion CR2. In addition, the analysis device 10d generates a graph GR on the basis of the image selected.

As described above, the analysis device 10d includes the information acquiring unit. The analysis device 10d can acquire results of processing requiring a large information-processing load and performed by the other device. In addition, the analysis device 10d can select an image that meets the condition from among a large number of cell images BP on the basis of the results of processing acquired from the other device. This enables the analysis device 10d to be configured with a low cost.

Note that a program for achieving functions of a given constituent portion in the analysis device 10, the analysis device 10a, the analysis device 10b, the analysis device 10c, and the analysis device 10d, each of which has been described above, may be recorded (stored) in a computer-readable recording medium (storage medium), and a computer system may be caused to read the program to cause the computer system to execute the program. Note that a term "computer system" as used herein includes an Operating System (OS) or hardware such as a peripheral unit. Moreover, the term "computer-readable recording medium" as used herein represents a portable recording medium such as a flexible disk, a magneto-optical disk, a Read Only Memory (ROM), and a Compact Disc (CD)-ROM, and a storage device such as a hard disk drive that is built in with the computer system. Further, the term "computer-readable recording medium" may also include a medium that holds the program for a certain period of time, such as a volatile memory (Random Access Memory: RAM) built into a computer system that is a server or a client when the program is transmitted over a network such as the Internet or a communication line such as a phone line.

In addition, the above-described program may be transmitted from the computer system in which the program is stored in a storage device or the like, to another computer system, via a transmission medium or by transmission waves in the transmission medium. Here, the "transmission medium" that transmits the program represents a medium having a function to transmit information, such as the Internet or another network (communication network) and a communication line such as a telephone line.

Further, the above-described program may be a program for achieving a part of the above-described functions. Moreover, the above-described program may be achieved by a combination of this program with a program already recorded in the computer system, namely, by a so-called differential file (differential program).

Note that various aspects of the embodiments described above may be combined as appropriate. Moreover, some of the component parts may be removed. Moreover, to the extent permissible by law, all publications and the US patent documents related to the devices or the like used in the embodiments and modification examples as described above are incorporated herein by reference.

REFERENCE SIGNS LIST

1 Cell observation system
10, 10a, 10b, 10c, 10d Analysis device
20 Microscopic device
21 Electromotive stage
22 Image capturing unit
30 Display unit
40 Manipulation unit 100 Computing unit
101 Cell-image acquiring unit
102 Feature value calculating unit
103 Noise-component eliminating unit
104 Correlation extracting unit
200 Storage unit
201 Type storage unit
202 Experiment-condition storage unit
203 Cell-image storage unit
300 Display control unit
400, 400a, 400b, 400c, 400d Cell-image selecting unit
401 Correlation selecting unit
402 Image selecting unit
403 Feature value selecting unit
404, 404a, 404b First image selecting unit
405 Image selecting unit
406 Second image selection criterion
407 Graph generating unit
500 Operation detecting unit

The invention claimed is:

1. An image selecting apparatus comprising:
a correlation selecting unit configured to select a desired correlation among a plurality of correlations between constituent elements calculated from a change in a feature value concerning constituent elements that form a cell, and
an image selecting unit configured to select an image, which includes a constituent element corresponding to the desired correlation, based on the selected desired correlation.

2. The image selecting apparatus according to claim 1, wherein the change in the feature value concerning the constituent element is calculated from an image in which a cell is captured.

3. The image selecting apparatus according to claim 2, wherein the change in the feature value concerning the constituent element is calculated from a plurality of images in which a cell is captured.

4. The image selecting apparatus according to claim 3, wherein the image selecting apparatus associates the change in the feature value concerning the constituent element and the plurality of images, and displays an image corresponding to a change in a feature value concerning the selected constituent element.

5. The image selecting apparatus according to claim 3, wherein the image selecting apparatus associates a value of the feature value concerning the constituent element and the image in which the cell is captured, and displays an image corresponding to the value of the feature value.

6. The image selecting apparatus according to claim 1, wherein the image selecting unit selects the image based on information of the image within the plurality of images.

7. The image selecting apparatus according to claim 6, wherein the information of the image includes at least one piece of information on a number of cells in the image, a shape of the cell, abnormality of the cell, presence or absence of abnormality, contrast, a number of the constituent element, a shape of the constituent element and a difference between a focal position.

8. The image selecting apparatus according to claim 6, wherein the image selecting apparatus calculates the change in the feature value concerning the constituent element of the cell from the image selected by the image selecting unit.

9. The image selecting apparatus according to claim 4, wherein the image selecting unit selects an image different from the selected image from the plurality of images based on the selected image selected by the image selecting unit.

10. The image selecting apparatus according to claim 9, wherein the image selecting apparatus selects the image different from the selected image through machine learning using the selected image.

11. The image selecting apparatus according to claim 1, wherein the change in the feature value concerning the constituent element is based on a value of the feature value at a first time and a value of the feature value at a second time, and the image selecting unit selects a first cell image, which is obtained at the first time, and a second cell image which is obtained at the second time.

12. The image selecting apparatus according to claim 11, wherein the image selecting unit selects an image of which shape resembles the first cell image and the second cell image.

13. The image selecting apparatus according to claim 12, wherein the image selecting unit displays the first cell image and the second cell image.

14. The image selecting apparatus according to claim 13, wherein, a value of the feature value at the first time and the image in which the cell is captured are associated with each other and a value of the feature value at the second time and the image in which the cell is captured are associated with each other, and the image selecting apparatus displays the selected first cell image corresponding to the value of the feature value at the first time and the selected second cell image corresponding to the value of the feature value at the second time.

15. The image selecting apparatus according to claim 2, wherein the change in the feature value concerning the constituent element include at least one of a change in luminosity, dispersion of luminosity, a change in area, a change of position, and a change in the number, within the image in which the cell is captured.

16. The image selecting apparatus according to claim 1, wherein the constituent element of the cell includes a first constituent element and a second constituent element, and
the desired correlation is a correlation between a change in a feature value concerning the first constituent element and a change in a feature value concerning the second constituent element.

17. The image selecting apparatus according to claim 16, wherein the correlation selecting unit selects the desired correlation by selecting the first constituent element and the second constituent element.

18. The image selecting apparatus according to claim 16, wherein the correlation selecting unit selects the first correlation by selecting a feature value concerning the first constituent element and a feature value concerning the second constituent element.

19. The image selecting apparatus according to claim 1, wherein the cell is a biological cell or fixed cell.

20. The image selecting apparatus according to claim 1, wherein the constituent element includes at least one of a gene, protein, and an organelle.

21. The image selecting apparatus according to claim 2, wherein the image selecting apparatus changes the selected desired correlation based on the selected image selected by the image selecting unit.

22. The image selecting apparatus according to claim 21, wherein the image selecting apparatus changes the selected desired correlation to a correlation different from the desired correlation based on the selected image selected by the image selecting unit.

23. The image selecting apparatus according to claim 22, wherein the image selecting apparatus calculates the different correlation by using an image different from the image used for calculating the desired correlation.

24. The image selecting apparatus according to claim 1, wherein the change in the feature value occurs due to a stimulus applied to the cell.

25. The image selecting apparatus according to claim 1, comprising a controller configured to display the image selected by the image selecting unit as a display image.

26. An image selecting method, comprising the steps of:
   selecting a desired correlation among a plurality of correlations between constituent elements calculated from a change in a feature value concerning constituent elements that form a cell, and
   selecting an image, which includes a constituent element corresponding to the desired correlation, based on the selected desired correlation.

27. A non-transitory computer-readable medium storing an image selecting program, the program causing a computer to perform the steps of:
   selecting a desired correlation among a plurality of correlations between constituent elements calculated from a change in a feature value concerning constituent elements that form a cell, and
   selecting an image, which includes a constituent element corresponding to the desired correlation, based on the selected desired correlation.

28. A display apparatus comprising:
   a correlation selecting unit configured to select a desired correlation among a plurality of correlations between constituent elements calculated from a change in a feature value concerning constituent elements that form a cell,
   an image selecting unit configured to select an image, which includes a constituent element corresponding to the desired correlation, based on the selected desired correlation, and
   a display unit configured to display the selected image.

* * * * *